(12) United States Patent
McGaff

(10) Patent No.: US 12,134,593 B2
(45) Date of Patent: *Nov. 5, 2024

(54) METHOD FOR OXIDATION OF SULFUR-CONTAINING COMPOUNDS

(71) Applicant: WiSys Technology Foundation, Inc., Madison, WI (US)

(72) Inventor: Robert William McGaff, LaCrosse, WI (US)

(73) Assignee: WiSys Technology Foundation, Inc., Madison, WI (US)

( * ) Notice: Subject to any disclaimer, the term of this patent is extended or adjusted under 35 U.S.C. 154(b) by 921 days.

This patent is subject to a terminal disclaimer.

(21) Appl. No.: 17/268,311

(22) PCT Filed: Aug. 20, 2019

(86) PCT No.: PCT/US2019/047227
§ 371 (c)(1),
(2) Date: Feb. 12, 2021

(87) PCT Pub. No.: WO2020/041284
PCT Pub. Date: Feb. 27, 2020

(65) Prior Publication Data
US 2021/0332010 A1 Oct. 28, 2021

Related U.S. Application Data

(60) Provisional application No. 62/719,817, filed on Aug. 20, 2018.

(51) Int. Cl.
| | | |
|---|---|---|
| *C07C 319/30* | (2006.01) | |
| *B01J 31/18* | (2006.01) | |
| *C07C 319/24* | (2006.01) | |
| *C07D 333/76* | (2006.01) | |
| *C07F 15/02* | (2006.01) | |

(52) U.S. Cl.
CPC .......... *C07C 319/30* (2013.01); *B01J 31/183* (2013.01); *C07C 319/24* (2013.01); *C07D 333/76* (2013.01); *C07F 15/025* (2013.01); *B01J 2231/4294* (2013.01); *B01J 2231/70* (2013.01); *B01J 2531/842* (2013.01)

(58) Field of Classification Search
CPC ... C07C 319/20; C07C 319/34; C07F 15/025; C07D 333/76; B01T 2231/4294; B01T 2231/70; B01T 2531/842; B01J 2231/4294; B01J 2231/70; B01J 2531/842
See application file for complete search history.

(56) References Cited

U.S. PATENT DOCUMENTS

| | | |
|---|---|---|
| 3,505,210 A | 4/1970 | Wallace et al. |
| 8,986,638 B2 | 3/2015 | Ivanovic-burmazovic et al. |
| 10,065,980 B2 | 9/2018 | McGaff |
| 11,826,740 B2 | 11/2023 | Mcgaff |
| 2017/0022233 A1 | 1/2017 | Mcgaff |
| 2023/0040510 A1 | 2/2023 | Mcgaff |

OTHER PUBLICATIONS

"International Application Serial No. PCT US2019 047227, International Preliminary Report on Patentability mailed Mar. 4, 2021", 6 pages.
U.S. Appl. No. 15/217,350 U.S. Pat. No. 10,065,980, filed Jul. 22, 2016, Bridged Phthalocyanine- and Napththalocyanine-Metal Complex Catalysts and Methods of Using and Purifying the Same.
U.S. Appl. No. 17/861,715 U.S. Pat. No. 11,826,740, filed Jul. 11, 2022, Bridged Phthalocyanine- and Napththalocyanine-Metal Complex Catalysts for Oxidation Reactions.
"U.S. Appl. No. 17/861,715, Notice of Allowance mailed Jul. 24, 2023", 7 pgs.
"U.S. Appl. No. 15/217,350, Final Office Action mailed Dec. 14, 2017", 10 pgs.
"U.S. Appl. No. 15/217,350, Non Final Office Action mailed Jun. 12, 2017", 15 pgs.
"U.S. Appl. No. 15/217,350, Notice of Allowance mailed May 2, 2018", 8 pgs.
"U.S. Appl. No. 15/217,350, Response filed Mar. 14, 2018 to Final Office Action mailed Dec. 14, 2017", 15 pgs.
"U.S. Appl. No. 15/217,350, Response filed Sep. 12, 2017 to Non Final Office Action mailed Jun. 12, 2017", 12 pgs.
"International Application Serial No. PCT/US2019/047227, International Search Report mailed Nov. 18, 2019", 2 pgs.
"International Application Serial No. PCT/US2019/047227, Written Opinion mailed Nov. 18, 2019", 4 pgs.
Javadli, et al., "Desulfuization of Heavy Oil", vol. 1, pp. 3-19. DOI 10.1007/S13203-012-0006-6; Entire Document, (2012).
Joseph, et al., "Covalently Anchored Polymer Immobilized Co(II) Phthalocyanine as Efficient Catalyst for Oxidation of Mercpatans using Molecular Oxygen as Oxidant", Ind. Eng. Chem. Res. vol. 49, (2010), 6674-6677.
Kieler, Heidi M., et al., "Racemic iron(III) and cobalt(III) complexes containing a new pentadentate "helmet" phthalocyaninato ligand{", Chem. Commun., (2006), 3326-3328.

(Continued)

*Primary Examiner* — Timothy R Rozof
(74) *Attorney, Agent, or Firm* — Schwegman Lundberg & Woessner, P.A.

(57) ABSTRACT

Various embodiments disclosed relate to a method of oxidizing sulfur-containing compounds. The method involves contacting a sulfur-containing compound with a helmet phthalocyaninato-type catalyst in the presence of an oxidant. The present invention also provides a method of removing undesired sulfur-containing compounds from a fluid, such as natural gas, crude oil or an aqueous waste stream.

19 Claims, No Drawings

(56) References Cited

OTHER PUBLICATIONS

Kikukawa, Yuu, et al., "Facile one-pot preparation of thermally and photochemically convertible soluble precursors of copper phthalocyanine and naphthalocyaninew", Chem. Commun., 47, (2011), 8518-8520.
Peterson, Brian M., et al., "Oxidation of primary and secondary benzylic alcohols with hydrogen peroxide and tert-butyl hydroperoxide catalyzed by a "helmet" phthalocyaninato iron complex in the absence of added organic solventt", Dalton Trans., 43, (2014), 17899-17903.

METHOD FOR OXIDATION OF SULFUR-CONTAINING COMPOUNDS

CROSS-REFERENCE TO RELATED APPLICATION

This application is a U.S. National Stage Filing under 35 U.S.C. 371 from International Application No. PCT/US2019/047227, filed on Aug. 20, 2019, and published as WO 2020/041284 on Feb. 27, 2020, which application claims the benefit of priority to U.S. Provisional Patent Application Ser. No. 62/719,817 entitled "METHOD FOR OXIDATION OF SULFUR-CONTAINING COMPOUNDS," filed Aug. 20, 2018, the disclosures of which are incorporated herein in their entirety by reference.

BACKGROUND

Oxidation of sulfur-containing compounds is an important chemical process in the chemical, petroleum and energy industries. Sulfur-containing compounds commonly occur in fossil fuels and petroleum products as impurities which are difficult to remove. Such compounds can poison catalysts used in downstream processing and can generate pollutants, such as sulfur oxides, during fuel combustion. It can thus be desirable to remove sulfur-containing compounds from fuels prior to processing or combustion. At the same time, such compounds are an important source of sulfur-containing compounds useful for production of fine chemicals. Chemical transformation, such as oxidation, provides one approach for which otherwise difficult to remove sulfur-containing compounds can be accessed. Existing oxidation methods require use of undesirable organic solvents, elevated temperatures, expensive precious metals, toxic heavy metals, and environmentally harmful oxidants. There remains a need for a green, room-temperature oxidation of sulfur-containing compounds.

SUMMARY OF THE INVENTION

The present invention provides a method of oxidizing a sulfur-containing compound. In various embodiments, the method includes contacting the sulfur-containing compound with a helmet phthalocyaninato-type catalyst in the presence of an oxidant.

The present invention also provides a method of removing sulfur-containing compounds from a fluid. The method involves contacting the fluid with a helmet phthalocyaninato-type catalyst in the presence of an oxidant to produce an oxidized sulfur-containing compound; and then separating the oxidized sulfur-containing compound from the fluid.

In various embodiments, the methods of the present invention involve use of a helmet phthalocyaninato-type catalyst having the structure:

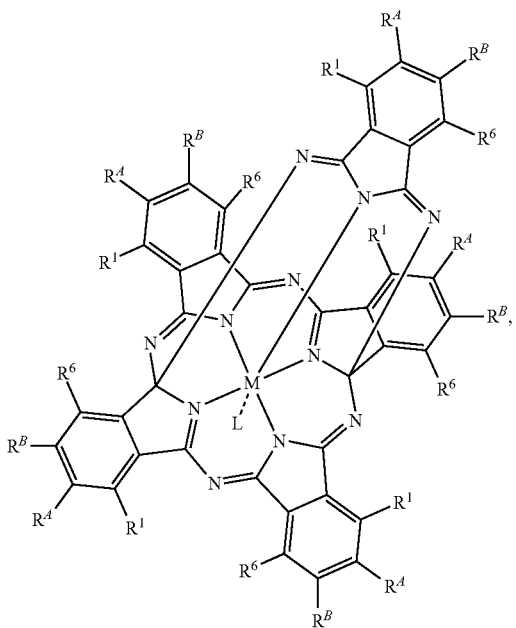

wherein
M is a metal,
axial ligand L is a solvent molecule or absent,
at each occurrence, $R^A$ and $R^B$ are independently chosen from —H, halide, an organic group, and a hydrophilic group, or $R^A$ and $R^B$ together form a fused aromatic ring with the ring upon which $R^A$ and $R^B$ are substituted, $R^A$ and $R^B$ together having the structure:

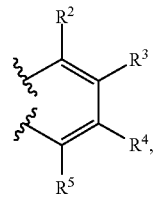

and
at each occurrence, $R^1$, $R^2$, $R^3$, $R^4$, $R^5$, and $R^6$ are each independently chosen from —H, halide, an organic group, a hydrophilic group, a salt thereof, a substituted or unsubstituted $(C_1$-$C_{50})$hydrocarbyl ester thereof, and a combination thereof.

Advantages, some of which are unexpected, are achieved by various embodiments of the present disclosure. In various embodiments, the present invention provides an efficient, economical, environmentally-friendly method of oxidizing sulfur-containing compounds. For example, various embodiments of the present invention can be performed at room temperature, thus providing the environmental and economic benefit of reducing energy consumption. As another example, various embodiments of the present invention can be performed without use of solvent or by use of environmentally-friendly solvents, e.g., water and alcohol. As another example, various embodiments of the present invention can be performed without the use of undesirable metals such as toxic heavy metals or expensive precious metals, thus resulting in a safer and more economic process.

DETAILED DESCRIPTION OF THE INVENTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "organic group" as used herein refers to any carbon-containing functional group. For example, an oxygen-containing group such as an alkoxy group, aryloxy group, arylalkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O(oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "heterocyclyl" as used herein refers to aromatic and non-aromatic ring compounds containing three or more ring members, of which one or more is a heteroatom such as, but not limited to, N, O, and S.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" or "hydrocarbyl" as used herein refers to a molecule or functional group, respectively, that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a$-$C_b)$hydrocarbyl, wherein a and b are integers and mean having any of a to b number of carbon atoms. For example, $(C_1$-$C_4)$hydrocarbyl means the hydrocarbyl group can be methyl $(C_1)$, ethyl $(C_2)$, propyl $(C_3)$, or butyl $(C_4)$, and $(C_0$-$C_b)$hydrocarbyl means in certain embodiments there is no hydrocarbyl group.

The term "thiol" means an organic compound having an —SH functional group. For example, an aromatic thiol is a compound which has an optionally substituted aromatic group linked directly to an —SH functional group. A non-aromatic thiol is a thiol which only contains non-aromatic moieties. An alkylthiol is a compound which has an optionally substituted alkyl group linked directly to an —SH functional group.

The term "thioether" means an organic compound having a divalent —S— moiety. Typically the thioether is a non-aromatic divalent —S— moiety but in some cases may include an aromatic divalent —S— moiety such as in the case of dibenzothiophene which has a —S— linkage which acts both like an aromatic thiophene moiety and also like a typical —S— linkage. In various embodiments, thioether may have the structure R—S—R, where each R group maybe the same or different and is independently substituted or unsubstituted alkyl, aryl or hetaryl.

The term "solvent" as used herein refers to a liquid that can dissolve a solid, liquid, or gas. Non-limiting examples of solvents are silicones, organic compounds, water, alcohols, ionic liquids, and supercritical fluids.

The term "room temperature" as used herein refers to a temperature of about 15° C. to 28° C.

The term "standard temperature and pressure" as used herein refers to about 20° C. and about 101 kPa.

Ambient temperature refers to a temperature around room temperature, corresponding to the indoor or outdoor environment in which the process is conducted, and in which its vessel is not subjected to additional external cooling or heating efforts. Ambient pressure refers to a pressure around 101 kPa (around sea-level) to about 90 kPa (at about a mile above sea level), corresponding to the pressure of the indoor or outdoor environment, and in which the vessel is not subjected to additional external pressurizing or depressurizing efforts. For example, ambient pressure can be $p=101325\times(1-2.25577\times10^{-5}\times h)^{5.25588}$ in which h is altitude above sea level in meters and p is pressure (Pa). Ambient air can have a molecular oxygen content of about 10 to about 30 vol %, about 15 to about 25 vol %, about 18 to about 23 vol %, about 19 vol % to about 22 vol %, about 20 vol % to about 22 vol %, about 20.5 vol % to 21.5 vol %, about 20 vol %, about 21 vol %, or about 22 vol %. In various embodiments, ambient air can have a molecular oxygen content of about 20.95% by volume.

In various embodiments, salts having a positively charged counterion can include any suitable positively charged counterion. For example, the counterion can be ammonium ($NH_4^+$), or an alkali metal such as sodium ($Na^+$), potassium ($K^+$), or lithium ($Li^+$). In some embodiments, the counterion can have a positive charge greater than +1, which can in some embodiments complex to multiple ionized groups, such as $Zn^{2+}$, $Al^{3+}$, or alkaline earth metals such as $Ca^{2+}$ or $Mg^{2+}$.

In various embodiments, salts having a negatively charged counterion can include any suitable negatively charged counterion. For example, the counterion can be a halide, such as fluoride, chloride, iodide, or bromide. In other examples, the counterion can be nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate. The counterion can be a conjugate base of any carboxylic acid, such as acetate or formate. In some embodiments, a counterion can have a negative charge greater than −1, which can in some embodiments complex to multiple ionized groups, such as oxide, sulfide, nitride, arsenate, phosphate, arsenite, hydrogen phosphate, sulfate, thiosulfate, sulfite, carbonate, chromate, dichromate, peroxide, or oxalate.

Catalyst

The present invention involves use of a catalyst. In various embodiments, the catalyst is a helmet phthalocyaninato-type catalyst, which may be optionally substituted with one or more functional groups. The catalyst can have any suitable purity, such as about 50 wt % pure to about 100 wt % pure, about 95 wt % pure to about 100 wt % pure, greater than 98 wt % pure, about 50 wt % pure or less, or equal to or greater than about 55 wt % pure, 60, 65, 70, 75, 80, 85, 86, 87, 88, 89, 90, 91, 92, 93, 94, 95, 95.5, 96, 96.5, 97, 97.5, 98, 98.5, 99, 99.2, 99.4, 99.6, 99.8, 99.9, 99.99, or about 99.999 wt % pure or more. In various embodiments, the catalyst has a chelated iron or cobalt atom, optionally substituted with a solvent ligand. The catalyst may be one, or a mixture of more than one, of the structures described herein.

The catalyst can have the structure:

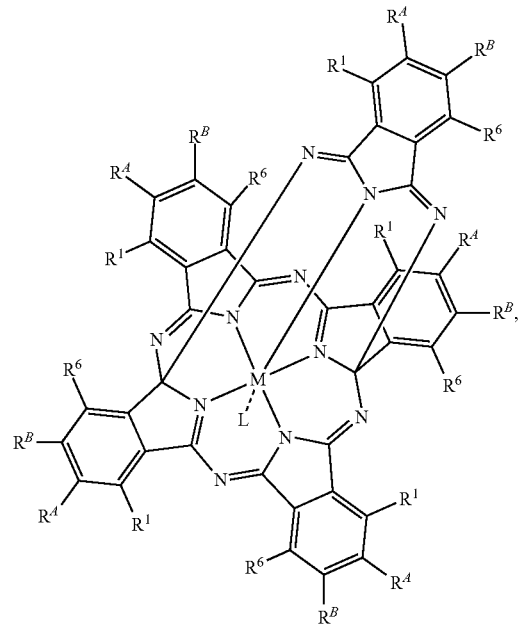

The variable M can be a metal. Herein metal atoms complexed with bridged phthalocyanine- and napthhthalocyanine structures are drawn showing no valence state. However, the metal atoms have the appropriate valence state that is consistent with the structure shown (e.g., II, III, IV, V). The variable M can be a Group VIII or IX transition metal. The variable M can be chosen from Co and Fe. The variable M can be Fe (e.g., Fe(III)). The axial ligand L can be a solvent molecule. The axial ligand L can be chosen from MeOH and $H_2O$. The axial ligand L can be $H_2O$.

At each occurrence, $R^A$ and $R^B$ can be independently chosen from —H, halide, an organic group, and a hydrophilic group, or $R^A$ and $R^B$ can together form a fused aromatic ring with the ring upon which $R^A$ and $R^B$ are substituted, $R^A$ and $R^B$ together having the structure:

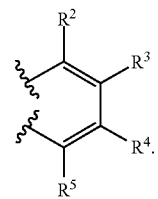

At each occurrence, $R^1$, $R^2$, $R^3$, $R^4$, $R^5$, and $R^6$ can be each independently chosen from —H, halide, an organic group, and a hydrophilic group. The hydrophilic group can be any suitable hydrophilic group. For example, at each occurrence, the hydrophilic group can be chosen from —C(O)OH, —O—C(O)OH, —P(O)(OH)$_2$, —OP(O)(OH)$_2$, —S(O)(O)OH, —OS(O)(O)OH, a salt thereof, a substituted or unsubstituted ($C_1$-$C_{50}$)hydrocarbyl ester thereof, and a combination thereof. The hydrophilic group can be —S(O)(O)OH.

In some embodiments, $R^A$ and $R^B$ can have the structure:

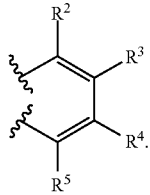

The variables $R^1$, $R^2$, $R^3$, $R^4$, $R^5$, and $R^6$ can be —H.

In some embodiments, $R^A$ and $R^B$ can have the structure:

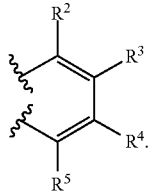

The variables $R^1$ and $R^6$ can be —H. At each occurrence, $R^2$, $R^3$, $R^4$, and $R^5$ can be independently chosen from —H and a hydrophilic group. At one more occurrences at least one of $R^2$, $R^3$, $R^4$, and $R^5$ can be a hydrophilic group.

In some embodiments, $R^A$ and $R^B$ can have the structure:

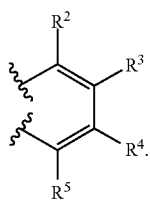

The variables $R^1$ and $R^6$ can be —H. At each occurrence, $R^2$, $R^3$, $R^4$, and $R^5$ can be independently chosen from —H and —S(O)(O)OH. At one more occurrences at least one of $R^2$, $R^3$, $R^4$, and $R^5$ can be —S(O)(O)OH.

In various embodiments, the variables $R^A$ and $R^B$ can be independently chosen from —H and a hydrophilic group. In various embodiments, at one or more occurrences at least one of $R^A$ and $R^B$ is a hydrophilic group. In various embodiments, at one or more occurrences at least one of $R^A$, $R^B$, $R^1$ and $R^6$ is a hydrophilic group. In various embodiments, at least one of $R^A$, $R^B$, $R^1$, $R^2$, $R^3$, $R^4$, $R^5$, and $R^6$ is a hydrophilic group.

In some embodiments, $R^1$, $R^A$, $R^B$, and $R^6$ are —H. The catalyst can have the structure:

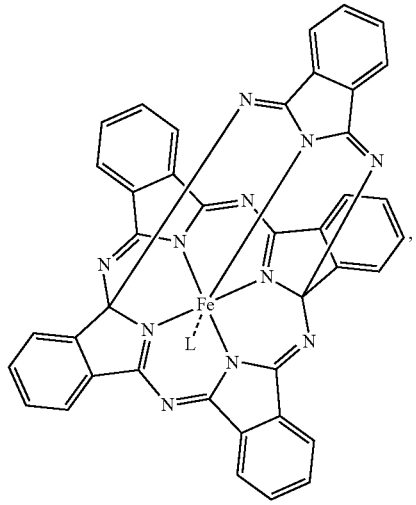

wherein axial ligand L can be $H_2O$.

Any suitable proportion of the catalyst composition can be the catalyst. For example, about 0.001 wt % to about 99.999 wt % of the catalyst composition can be the catalyst, or about 0.001 wt % or less, or equal to or less than about 0.01 wt %, 0.1, 1, 2, 3, 4, 5, 6, 8, 10, 15, 20, 25, 30, 35, 40, 45, 50, 55, 60, 65, 70, 75, 80, 85, 86, 88, 90, 91, 92, 93, 94, 95, 96, 97, 98, 99, 99.9, 99.99, or about 99.999 wt % can be catalyst.

The catalyst composition can further include a secondary catalyst having a different structure than the catalyst. The secondary catalyst can have the structure.

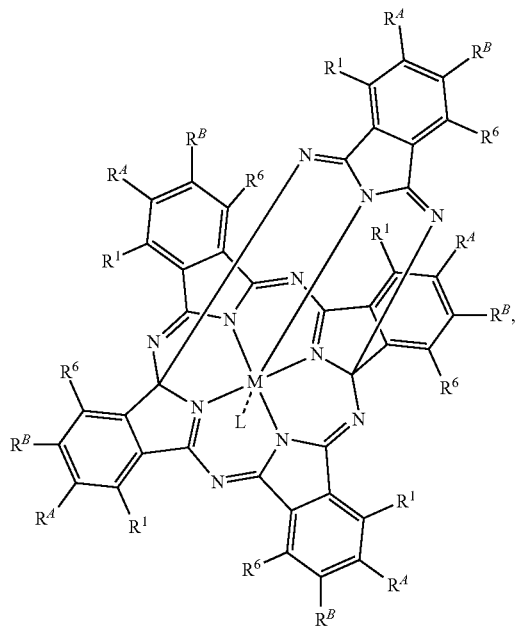

The variables M, L, $R^A$, $R^B$, $R^1$, $R^2$, $R^3$, $R^4$, $R^5$, and $R^6$ can correspond to any atom or group describes for the corresponding variables in the catalyst, so long as the secondary catalyst and the catalyst have different structure.

In various embodiment, the method is particularly valuable for separating a catalyst from a secondary catalyst wherein the catalyst and secondary catalyst have similar or the same structures with the exception of the identity of the axial ligand, L. For example, the method can be particularly valuable for separating a catalyst having an axial ligand L of H₂O from a secondary catalyst having an axial ligand L of MeOH. Thus, for example, the secondary catalyst can have the structure

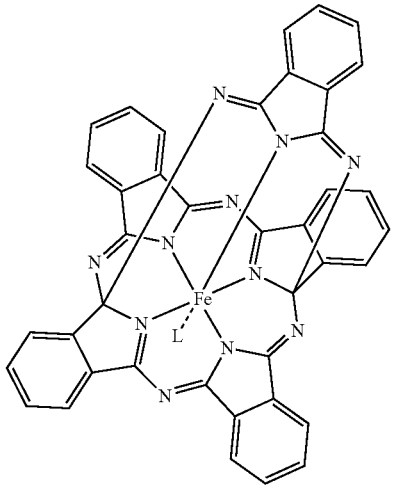

Axial ligand L in the secondary catalyst is MeOH.

The catalyst composition can include any suitable materials in addition to the catalyst, so long as the method can be performed as described herein. In various embodiments, the majority of the catalyst composition can be the catalyst and the secondary catalyst. For example, about 50 wt % to 100 wt % of the catalyst composition can be the catalyst and the secondary catalyst, or about 50 wt % or less, or greater than or equal to about 55 wt %, 60, 65, 70, 75, 80, 85, 86, 88, 90, 91, 92, 93, 94, 95, 96, 97, 98, 99, 99.9, 99.99, 99.999, or about 100 wt %. The purified catalyst can be substantially free of the secondary catalyst (e.g., can include 0 wt %, or less than about 0.0001 wt %, 0.001, 0.01, 0.1, 1, 2, 3, 4, 5, 10, 15, or less than about 20 wt %).

In various embodiments, the catalyst is:

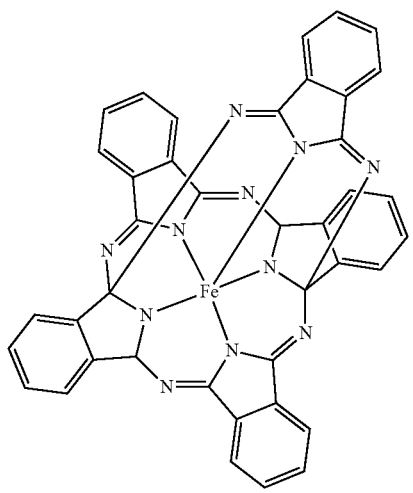

The subject application also provides use of a catalyst having the structure:

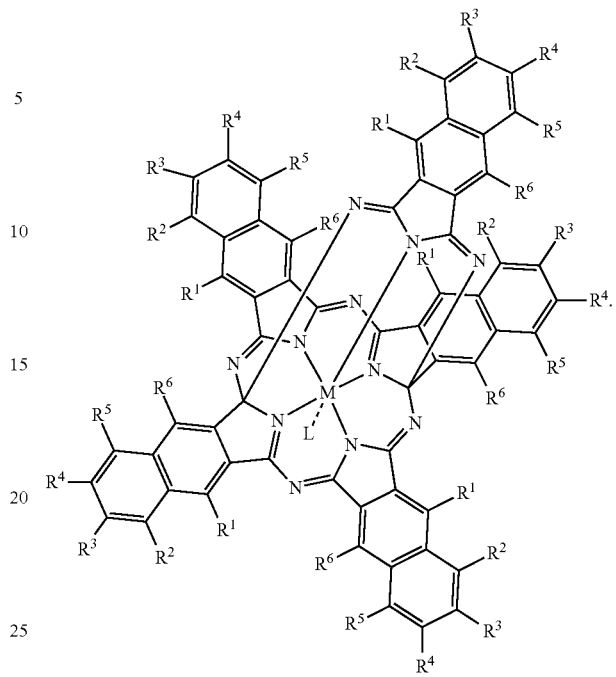

The variable M can be a metal. Herein metal atoms complexed with bridged phthalocyanine- and napththalocyanine structures are drawn showing no valence state. However, the metal atoms have the appropriate valence state that is consistent with the structure shown (e.g., II, III, IV, or V). The variable M can be a Group VIII or IX transition metal. The variable M can be chosen from Co and Fe. The variable M can be Fe (e.g., Fe(III)). The axial ligand L can be a solvent molecule. The axial ligand L can be chosen from MeOH and H₂O. The axial ligand L can be H₂O.

At each occurrence, $R^1$, $R^2$, $R^3$, $R^4$, $R^5$, and $R^6$ can be independently chosen from —H, halide, an organic group, and a hydrophilic group. The hydrophilic group can be any suitable hydrophilic group. For example, at each occurrence, the hydrophilic group can be chosen from —C(O)OH, —O—C(O)OH, —P(O)(OH)₂, —OP(O)(OH)₂, —S(O)(O) OH, —OS(O)(O)OH, a salt thereof, a substituted or unsubstituted (C₁-C₅₀)hydrocarbyl ester thereof, and a combination thereof. The hydrophilic group can be —S(O)(O)OH.

In some embodiments, $R^1$ and $R^6$ are —H, and at each occurrence, $R^2$, $R^3$, $R^4$, and $R^5$ are independently chosen from —H and a hydrophilic group. At one or more occurrences at least one of $R^2$, $R^3$, $R^4$, and $R^5$ can be a hydrophilic group (e.g., at least one of $R^2$, $R^3$, $R^4$, or $R^5$ in the molecule is a hydrophilic group).

In some embodiments, $R^1$ and $R^6$ are —H, and at each occurrence, $R^2$, $R^3$, $R^4$, and $R^5$ are independently chosen from —H and —S(O)(O)OH. At one or more occurrences at least one of $R^2$, $R^3$, $R^4$, and $R^5$ can be —S(O)(O)OH (e.g., at least one of $R^2$, $R^3$, $R^4$, or $R^5$ in the molecule can be —S(O)(O)OH).

Various embodiments of the present invention provide a method of oxidation including contacting an oxidizable starting material with the catalyst and an oxidant, to provide an oxidized product. The oxidizable starting material can be any suitable oxidizable starting material, such as a substituted or unsubstituted (C₁-C₅₀)hydrocarbyl alcohol, such as 2-pentanol, 1-pentanol, 2,4-dimethyl-3-pentanol, or isopropanol. The oxidant can be any suitable oxidant, such as tert-butylhydroperoxide, hydrogen peroxide, oxygen (e.g., from air, as a purified gas, or from hydrogen peroxide), and combinations thereof. In various embodiments, the contacting to provide an oxidized product can be carried out under solvent-containing or solvent-free conditions (e.g., wherein the reagents act as the solvent).

In various embodiments, the present invention provides a method of forming the catalyst. For example, the method can include combining a suitable M-containing reagent (e.g., Fe(OAc)$_2$) with a suitable material, such as 2,3-naphthalenedicarbonitrile, under conditions sufficient to produce the catalyst.

In various embodiments, the present invention provides a method of forming a derivatized catalyst. The method can include adding a hydrophilic group to the catalyst, such as by electrophilic aromatic substitution. The method can include adding to the catalyst one or more of —C(O)OH, —O—C(O)OH, —P(O)(OH)$_2$, —OP(O)(OH)$_2$, —S(O)(O)OH, —OS(O)(O)OH, a salt thereof, and a substituted or unsubstituted (C$_1$-C$_{50}$)hydrocarbyl ester thereof. The method can include adding to the catalyst —S(O)(O)OH, such as via treatment with sulfuric acid.

In various embodiments, the derivatized catalyst can have a greater water solubility than the un-derivatized catalyst, due to the added one or more hydrophilic groups. Various embodiments of the present invention provide a method of oxidation including contacting a suitable oxidizable starting material, a suitable oxidant, the derivatized catalyst, and water.

In various embodiments the catalyst has the structure:

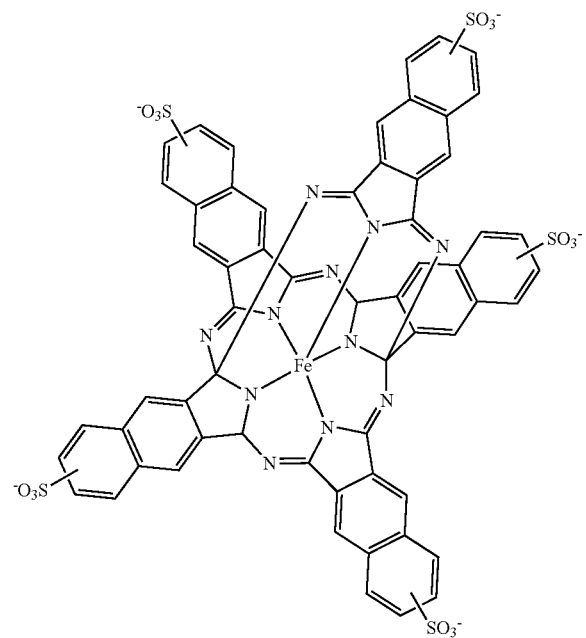

in the form of a free acid, sodium salt, or other salt thereof.

In various embodiments, the present invention involves use of a purified catalyst. The purified catalyst may be any catalyst described herein. The catalyst can be purified by any suitable means. In various embodiments, the catalyst is purified via a method provided in US Patent Application No. 2017/0022233 A1, which is incorporated by herewith in its entirety. In some embodiments, the purified catalyst can exhibit certain properties not shown by the catalyst under impure conditions. For example, in some embodiments, the purified catalyst can have exhibit different solubilities in various solvents, as compared to the catalyst in impure conditions. The purified catalyst can have any suitable purity, such as about 80 wt %-about 100 wt % pure, about 95 wt % to about 100 wt % pure, about 98 wt % to about 100 wt % pure, or about 80 wt % pure or less, or equal to or greater than about 81 wt %, 82, 83, 84, 85, 86, 87, 88, 89, 90, 91, 92, 93, 94, 95, 96, 97, 98, 99, 99.9, 99.99, or about 99.999 wt % pure or more.

For example, the catalyst can have the structure:

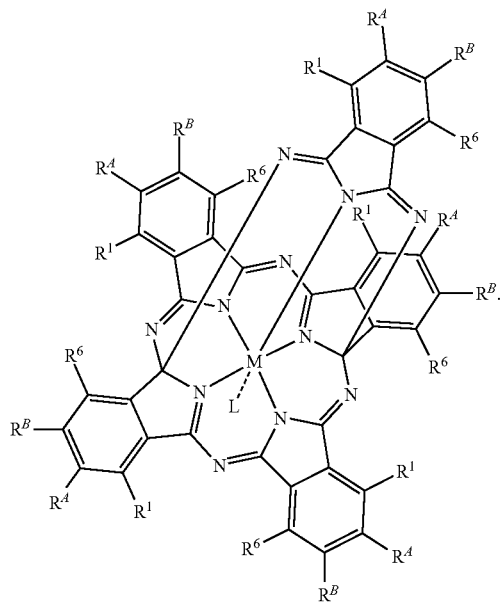

The variable M can be a metal. Herein metal atoms complexed with bridged phthalocyanine- and napththalocyanine structures are drawn showing no valence state. However, the metal atoms have the appropriate valence state that is consistent with the structure shown (e.g., II, III, IV, V). The variable M can be a Group VIII or IX transition metal. The variable M can be chosen from Co and Fe. The variable M can be Fe (e.g., Fe(III)). The axial ligand L can be a solvent molecule. The axial ligand L can be chosen from MeOH and H$_2$O. The axial ligand L can be H$_2$O.

At each occurrence, R$^A$ and R$^B$ can be independently chosen from —H, halide, an organic group, and a hydrophilic group, or R$^A$ and R$^B$ can together form a fused aromatic ring with the ring upon which R$^A$ and R$^B$ are substituted, R$^A$ and R$^B$ together having the structure:

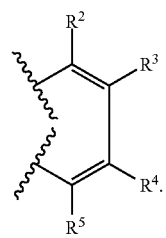

At each occurrence, R$^1$, R$^2$, R$^3$, R$^4$, R$^5$, and R$^6$ can be each independently chosen from —H, halide, an organic group, and a hydrophilic group. The hydrophilic group can be any suitable hydrophilic group. For example, at each occurrence, the hydrophilic group can be chosen from —C(O)OH, —O—C(O)OH, —P(O)(OH)$_2$, —OP(O)(OH)$_2$, —S(O)(O)OH, —OS(O)(O)OH, a salt thereof, a substituted or unsubstituted (C$_1$-C$_{50}$)hydrocarbyl ester thereof, and a combination thereof. The hydrophilic group can be —S(O)(O)OH.

In some embodiments, R$^A$ and R$^B$ can have the structure:

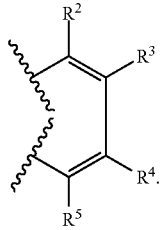

The variables R$^1$, R$^2$, R$^3$, R$^4$, R$^5$, and R$^6$ can be —H.

In some embodiments, R$^A$ and R$^B$ can have the structure:

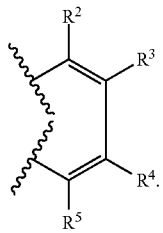

The variables R$^1$ and R$^6$ can be —H. At each occurrence, R$^2$, R$^3$, R$^4$, and R$^5$ can be independently chosen from —H and a hydrophilic group. At one more occurrences at least one of R$^2$, R$^3$, R$^4$, and R$^5$ can be a hydrophilic group.

In some embodiments, R$^A$ and R$^B$ can have the structure:

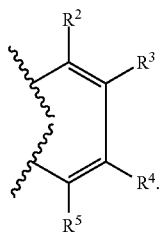

The variables R$^1$ and R$^6$ can be —H. At each occurrence, R$^2$, R$^3$, R$^4$, and R$^5$ can be independently chosen from —H and —S(O)(O)OH. At one more occurrences at least one of R$^2$, R$^3$, R$^4$, and R$^5$ can be —S(O)(O)OH.

In various embodiments, the variables R$^A$ and R$^B$ can be independently chosen from —H and a hydrophilic group. In various embodiments, at one or more occurrences at least one of R$^A$ and R$^B$ is a hydrophilic group. In various embodiments, at one or more occurrences at least one of R$^A$, R$^B$, Wand R$^6$ is a hydrophilic group. In various embodiments, at least one of R$^A$, R$^B$, R$^1$, R$^2$, R$^3$, R$^4$, R$^5$, and R$^6$ is a hydrophilic group.

In some embodiments, R$^1$, R$^A$, R$^B$, and R$^6$ are —H. The catalyst can have the structure:

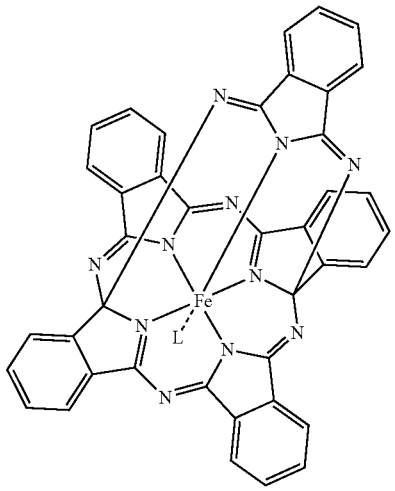

Axial ligand L can be H$_2$O.

In various embodiments, the purified catalyst has the structure:

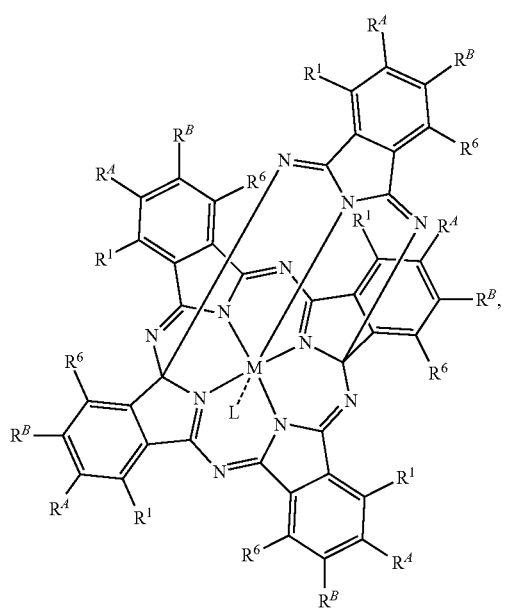

wherein M is a metal, axial ligand L is a solvent molecule, at each occurrence, R$^A$ and R$^B$ are independently chosen from —H, halide, an organic group, and a hydrophilic group, or R$^A$ and R$^B$ together form a fused aromatic ring with the ring upon which R$^A$ and R$^B$ are substituted, R$^A$ and R$^B$ together having the structure:

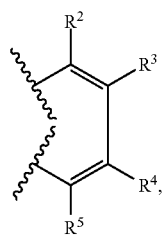

at each occurrence, $R^1$, $R^2$, $R^3$, $R^4$, $R^5$, and $R^6$ are each independently chosen from —H, halide, an organic group, and a hydrophilic group, wherein at each occurrence, the hydrophilic group is independently chosen from —C(O)OH, —O—C(O)OH, —P(O)(OH)$_2$, —OP(O)(OH)$_2$, —S(O)(O)OH, —OS(O)(O)OH, a salt thereof, a substituted or unsubstituted ($C_1$-$C_{50}$)hydrocarbyl ester thereof, and a combination thereof, and the purified catalyst is about 95 wt % pure to about 100 wt % pure.

In various embodiments, the catalyst can have the structure:

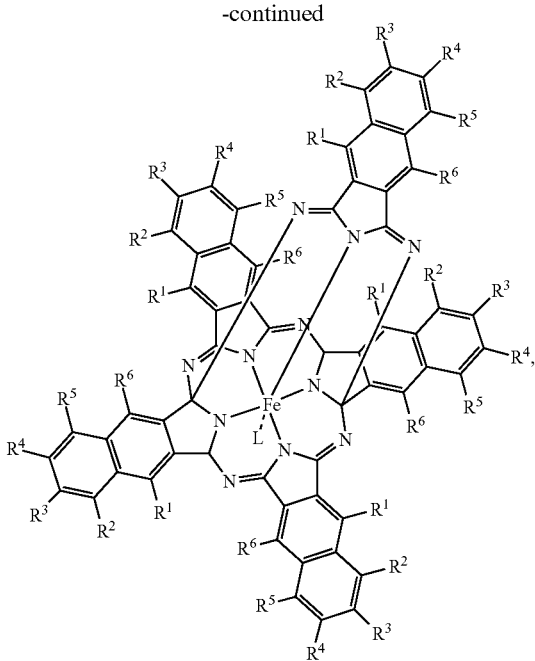

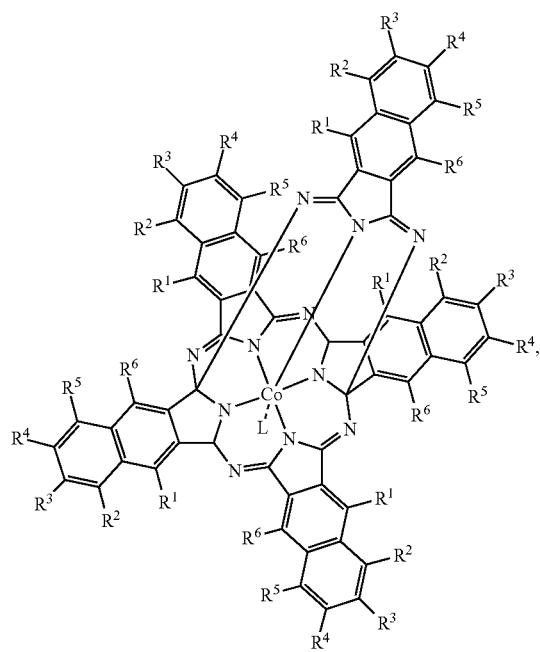

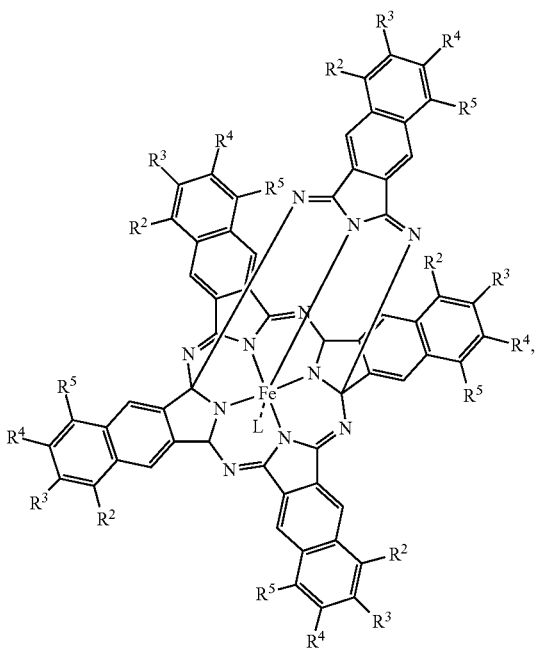

19
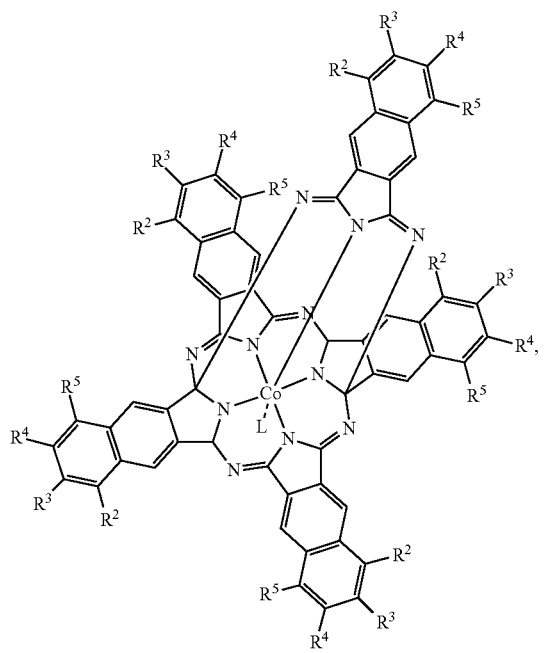
20
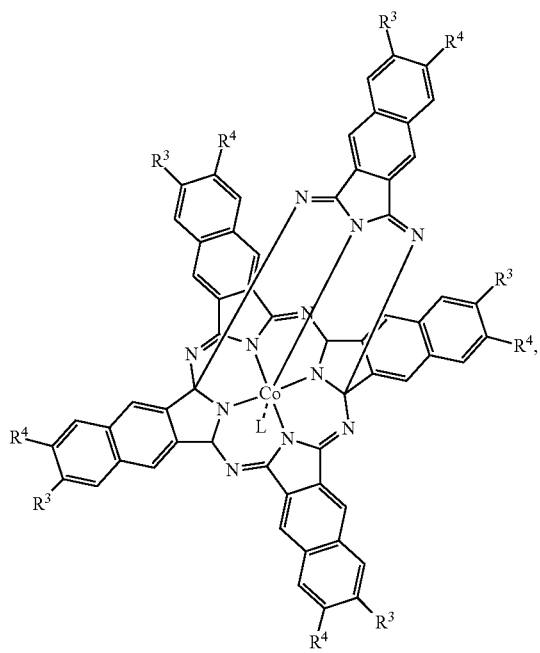
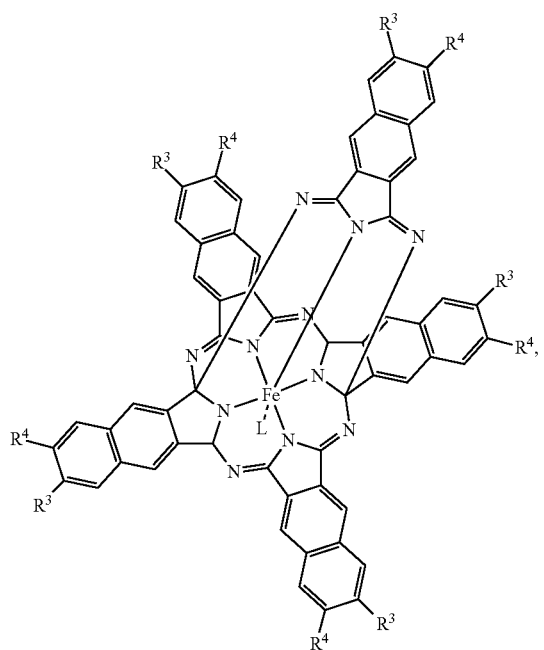
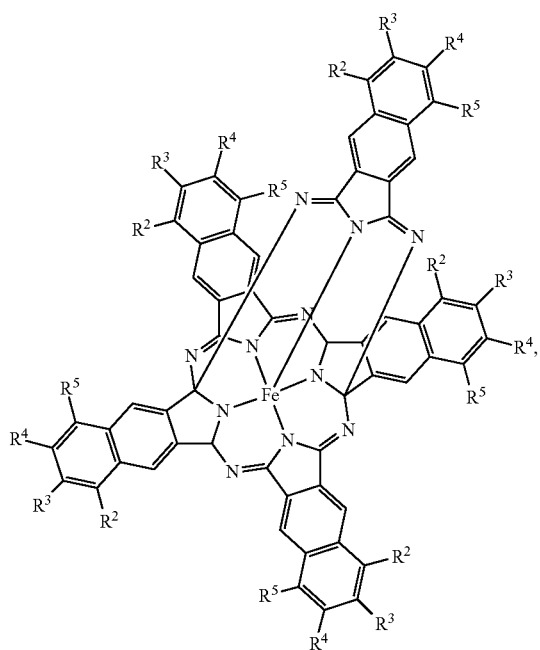

-continued

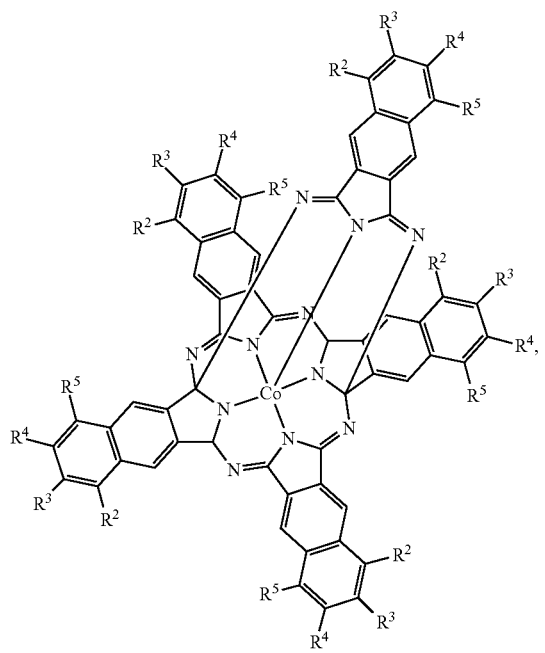

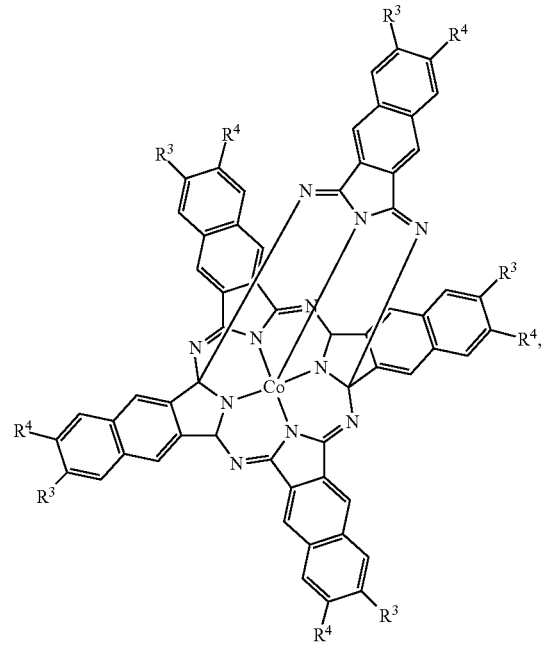

or a mixture thereof, wherein at each occurrence, $R^1$, $R^2$, $R^3$, $R^4$, $R^5$, and $R^6$, if present, can be each independently chosen from —H, halide, an organic group, and a hydrophilic group, and L is a solvent molecule.

In various further embodiments, the purified catalyst has an axial ligand L chosen from MeOH and $H_2O$. In various embodiments, the purified catalyst has at one more occurrences at least one of $R^2$, $R^3$, $R^4$, and $R^5$ is —S(O)(O)OH. In various embodiments, the purified catalyst has the structure:

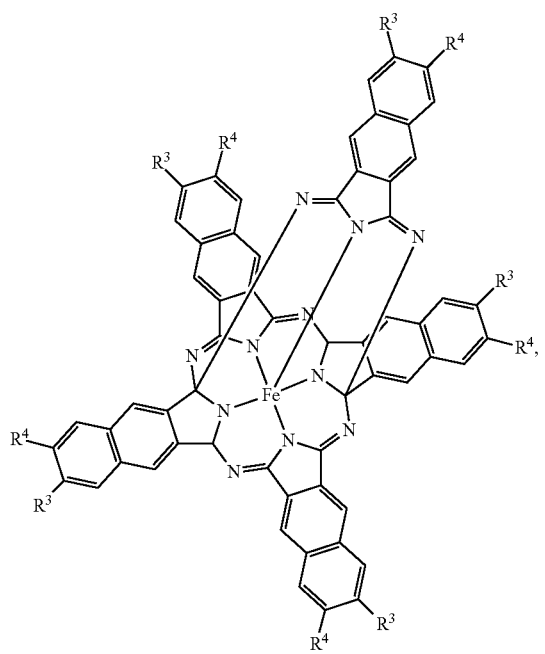

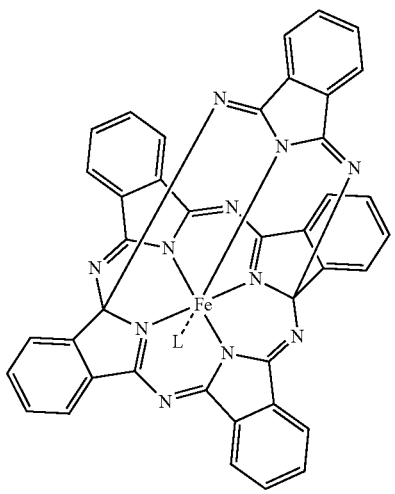

wherein axial ligand L is $H_2O$.

In various embodiments, the catalyst can have the structure:
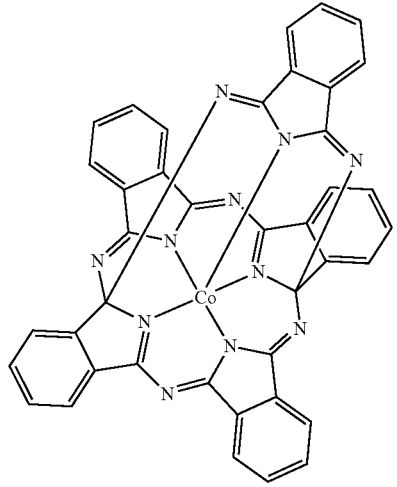
or
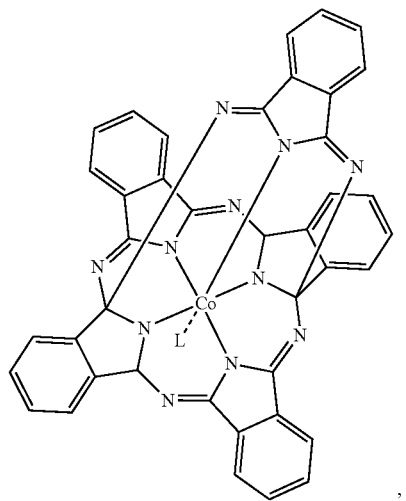
wherein axial ligand L is H₂O.
In various embodiments, the catalyst can have the structure:
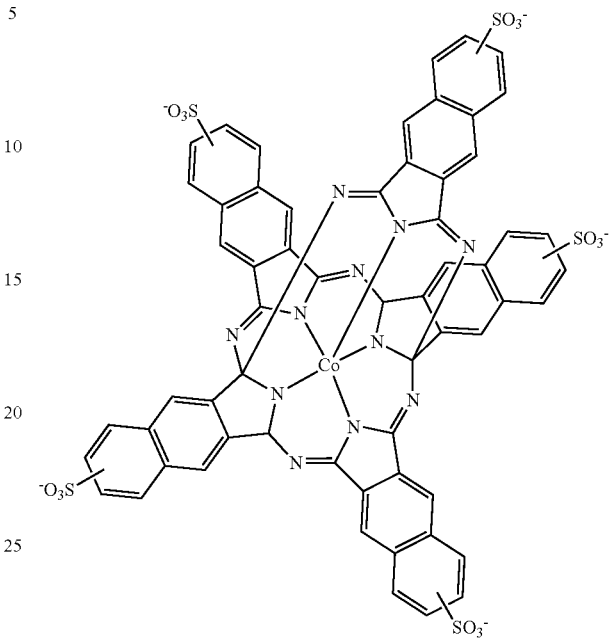
in the form of a free acid, sodium salt or other salt thereof.
In various embodiments, the catalyst can have the structure:
in the form of a free acid, sodium salt or other salt thereof.

In various embodiments, the catalyst can have the structure:
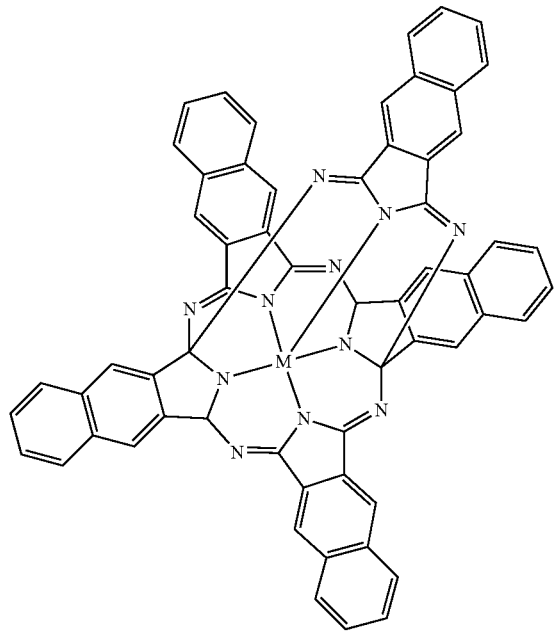
wherein M is Co or Fe.
For example, the catalyst can have the structure:
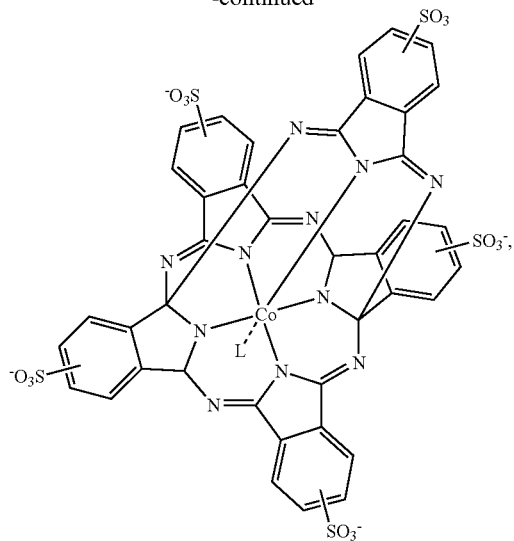
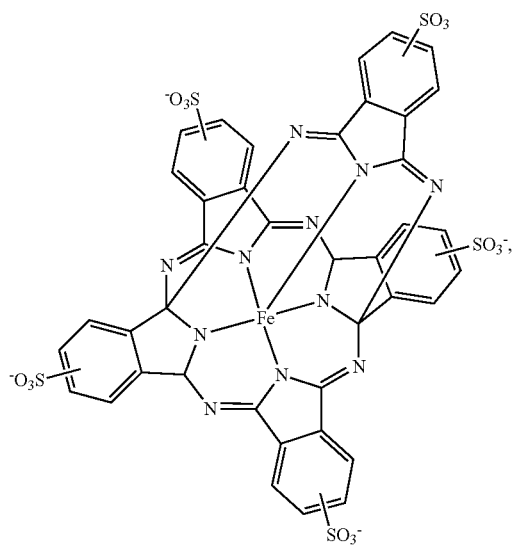
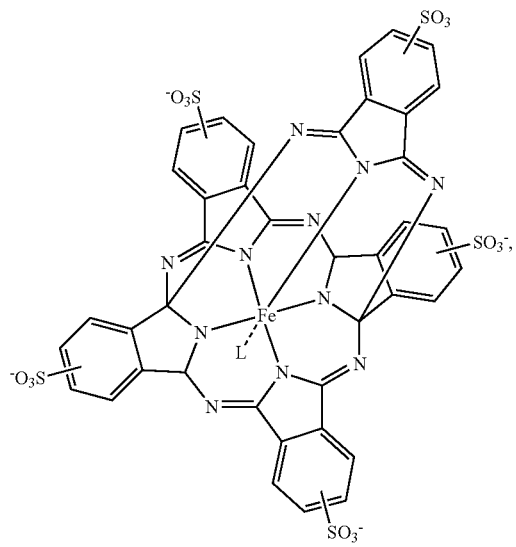
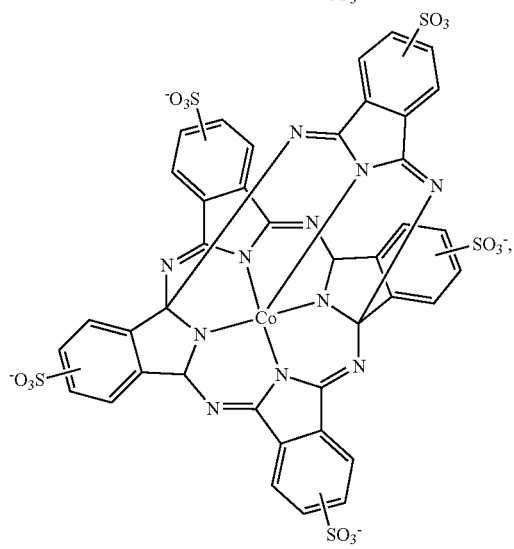
in the form of a free acid, sodium salt or other salt thereof.

In some embodiments, the catalyst can have the structure:
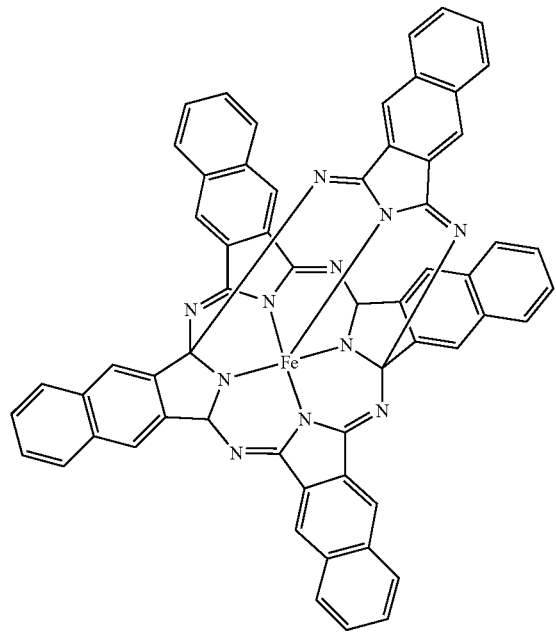
,
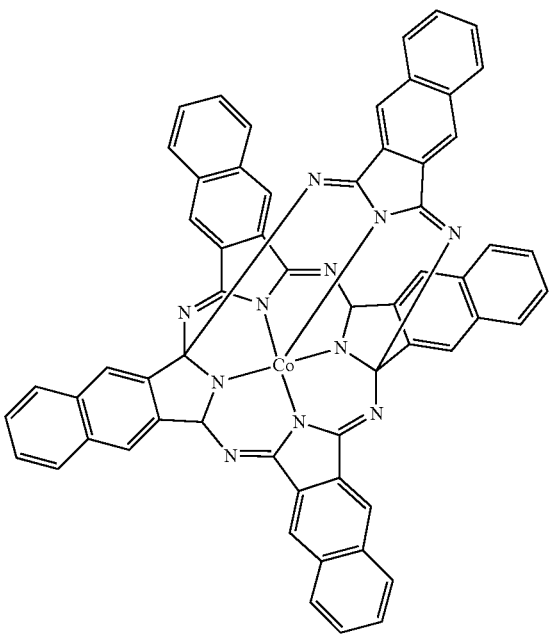
,
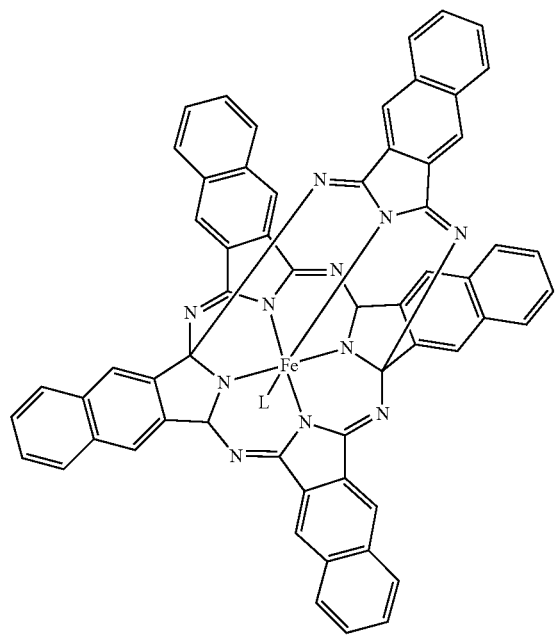
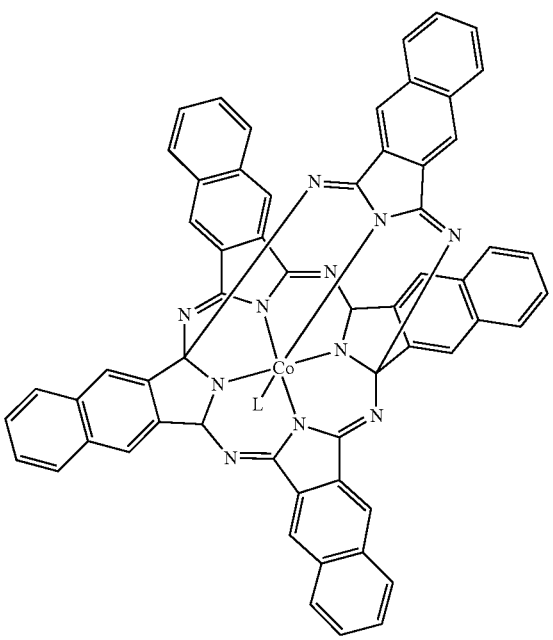
,
or a mixture thereof.

In some embodiments, the catalyst can have the structure:

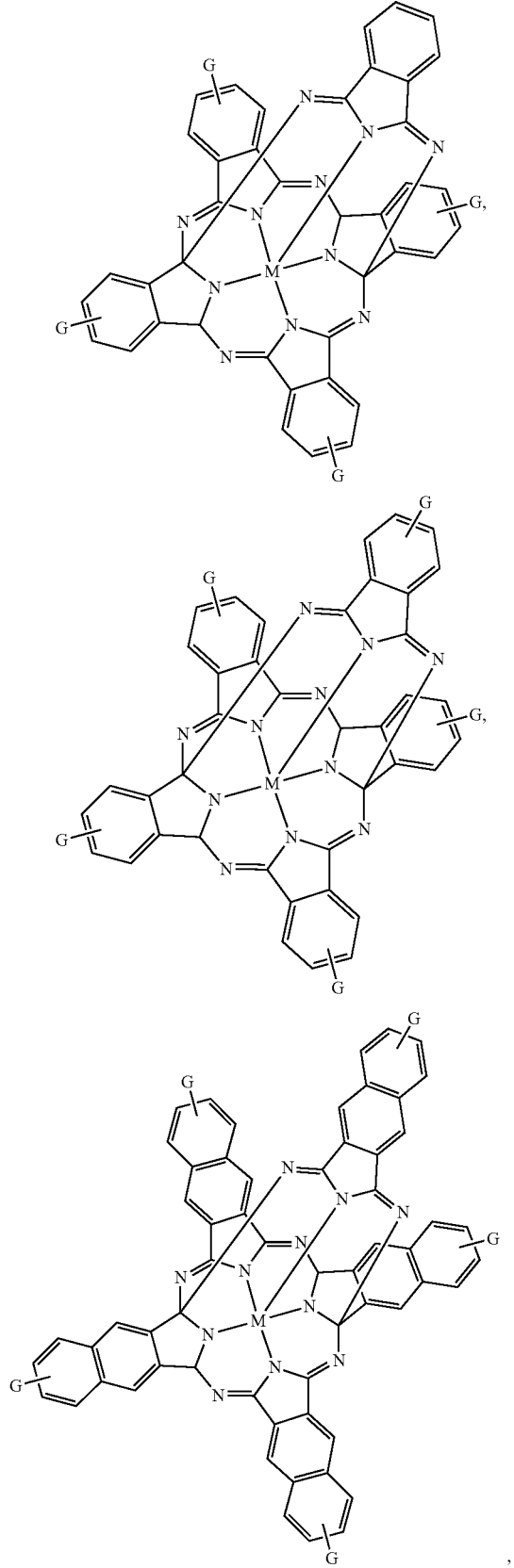

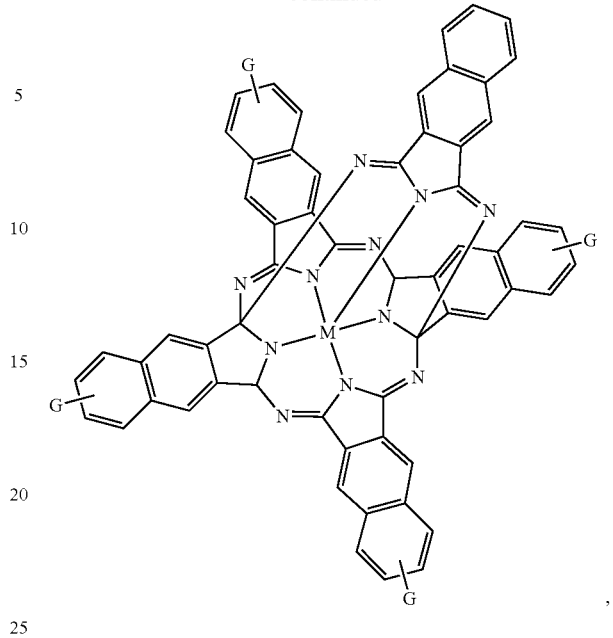

, or wherein M is Fe or Co, and G is a hydrophilic group.

In various embodiments, the catalyst is a homogeneous catalyst and in other embodiments the catalyst is a heterogenous catalyst. For example, in some embodiments, the catalyst may be soluble in one or more of the sulfur-containing starting material, solvent and fluid involved in the reaction mixture. In further embodiments, the catalyst is not soluble in the reaction mixture or any of the components thereof. Some embodiments involve a combination of homogeneous and heterogeneous catalysts.

The catalyst may be immobilized on a solid support. The solid support can be any suitable solid support. For example, the solid support may comprise silica, silica gel, zeolite, ion-exchange resin, or sulfonated polystyrene.

In various embodiments, the catalyst can be the catalyst described in U.S. Pat. No. 10,065,980, the disclosure of which is incorporated herein in its entirety by reference.

Method of Oxidizing Sulfur-containing Compounds

The present invention provides a method of oxidizing sulfur-containing compounds. The method can include contacting an oxidizable sulfur-containing starting material with any embodiment of a catalyst described herein and an oxidant. The contacting of the oxidizable starting material, the catalyst, and the oxidant, provides an oxidized product. The catalyst in various embodiments can be any of the catalysts described herein.

In various embodiments, the contacting step is performed at room temperature.

In various embodiments, the contacting step is performed at ambient pressure.

In various embodiments, the oxidant is molecular oxygen in ambient air or hydrogen peroxide.

The contacting to provide an oxidized product can be carried out, in various embodiments, under solvent-free conditions. Under such solvent-free conditions, the liquid reagents (e.g., the oxidizable starting material and the oxidized product) are suitable for dissolving the catalyst and the oxidizing agent. For example, in various embodiments, the catalyst (e.g., the purified catalyst) is dissolved in a solvent comprising or consisting of the starting material to be oxidized. In various embodiments, the catalyst is dissolved in water, alcohols, or a mixture thereof. In some such embodiments, oxidation is carried out without the addition of any other solvents. In some embodiments, the catalyst remains undissolved and operates catalytically from a heterogeneous solution. In various embodiments, the solvents are one or more of water and ethanol. In various embodiments, the solvent comprises or consists of water, ethanol, the starting material to be oxidized, or any combination thereof. In various embodiments, the solvents are one or more of acetonitrile and dichloromethane. In various embodiments, the solvent includes a linear or branched chain $C_1$-$C_{10}$ alcohol.

The oxidant can be any suitable oxidant. The oxidant can be chosen from tert-butylhydroperoxide, hydrogen peroxide, molecular oxygen in ambient air and combinations thereof.

The present invention provides a method of removing sulfur-containing compounds (e.g., mercaptans) from a mixture using ambient air as an oxidant, at ambient temperature and pressure.

Method of Removing Sulfur-Containing Compounds from a Fluid

The present invention provides a method of removing sulfur-containing compounds from a fluid. The method can include contacting the fluid with a catalyst in the presence of an oxidant to produce an oxidized sulfur-containing compound and separating the oxidized sulfur-containing compound from the fluid. The contacting of the oxidizable starting material, the catalyst, and the oxidant, provides an oxidized product. The catalyst in various embodiments can be any of the catalysts described herein.

In various embodiments, the contacting step is performed at room temperature.

In various embodiments, the contacting step is performed at ambient pressure.

In various embodiments, the oxidant is molecular oxygen in ambient air or hydrogen peroxide.

The fluid can be for example any fluid which comprises a sulfur-containing compound. In various embodiments, the fluid is a fossil fuel, natural gas, petroleum, coal, crude oil or refined oil. In various embodiments, the fluid is an aqueous waste stream, an exhaust gas waste stream, a combustion exhaust stream, or a fluid containing combustion and soot particulate.

The catalyst (e.g., the purified catalyst) and the fluid can further be additionally mixed with a solvent. In various embodiments, the solvent is water, alcohols, or a mixture thereof. In some such embodiments, oxidation is carried out without the addition of any other solvents. In some embodiments, the catalyst remains undissolved and operates catalytically from a heterogeneous solution. In various embodiments, the solvents are one or more of water and ethanol. In various embodiments, the solvent comprises or consists of water, ethanol, the starting material to be oxidized, or any combination thereof. In various embodiments, the solvents are one or more of acetonitrile and dichloromethane. In various embodiments, the solvent includes a linear or branched chain $C_1$-$C_{10}$ alcohol.

In various embodiments of the method, the oxidation step converts a sulfur-containing compound which cannot be readily filtered, distilled, extracted or otherwise separated out, into an oxidized sulfur-containing compound which is more easily separated. For example, the sulfur-containing compound starting material may have a boiling point, a chromatographic retention time, solubility or a particle size which overlapping with boiling points, chromatographic retention times, or a particle sizes of other components in the fluid. As a further example, the oxidized sulfur-containing compound product has a different boiling point, chromatographic retention time, solubility or a particle size which is non-overlapping or less-overlapping with the other components of the fluid. Thus, in various embodiments, the oxidized product is more easily separated than the starting material or can be separated where the starting material could not be.

Separating the oxidized sulfur-containing compound from the fluid need not be limited to any particular method. In various embodiments, the separating step comprising performing extraction. For example, the separating step can involve mixing the fluid with an immiscible solvent having greater affinity than the fluid for the oxidized sulfur-containing compound. In various embodiments, the separating step comprises filtration, distillation, or chromatography of the fluid containing the oxidized sulfur-containing compound.

Oxidizable Sulfur-Containing Starting Material

The oxidizable starting material can be any suitable oxidizable sulfur-containing starting material.

In various embodiments, the sulfur-containing compound is an aromatic thiol, a non-aromatic thiol or a thioether. The sulfur-containing compound can be a substituted or unsubstituted alkylthiol. The thioether may be a cyclic thioether, a thioether having two of the same substituents or two different substituents. The sulfur-containing compound can be a thiophene, including a benzothiophene and a dibenzothiophene.

In various embodiments, the sulfur-containing compound has the structure

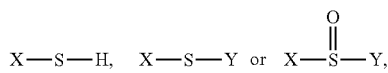

wherein each of X and Y is independently $C_1$-$C_{20}$ alkyl, $C_6$-$C_{10}$ aryl or $C_2$-$C_{10}$ heteroaryl, each of which may be optionally substituted, and X and Y may be linked so as to form a ring.

The oxidizable starting material can be a substituted or unsubstituted ($C_1$-$C_{50}$)hydrocarbyl thiol. The oxidizable starting material can be 2-pentanthiol, 1-pentanthiol, and 2,4-dimethyl-3-pentanthiol. The oxidizable starting material can be 2-mercaptoethanol. The oxidizable starting material can be dibenzothiophene.

The sulfur-containing compound can be

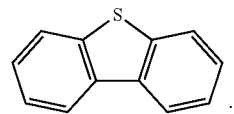 [SMILES: c1ccc2c(c1)sc1ccccc12]

The sulfur-containing compound can be

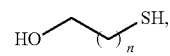

wherein n is 0-10.

The sulfur-containing compound can be

wherein m is 0-10.

The reaction can correspond to the scheme:

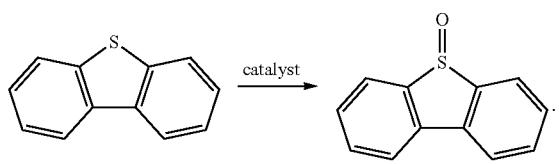 [SMILES: c1ccc2c(c1)sc1ccccc12 ; O=S1c2ccccc2-c2ccccc21]

The reaction can correspond to the scheme:

wherein m is 0-10.

The reaction can correspond to the scheme:

wherein n is 0-10.

The sulfur-containing compound can be methyl mercaptan, ethyl mercaptan, n-propyl mercaptan, i-propyl mercaptan, 1-butyl mercaptan, 2-butyl mercaptan, i-butyl mercaptan, t-butyl mercaptan, 1-pentyl mercaptan, 2-pentyl mercaptan, or 3-pentyl mercaptan. The sulfur-containing compound can be an organic compound containing one or more sulfur atoms that is a contaminant in a petroleum oil, a natural gas, or coal.

In various embodiments, the sulfur-containing compound can be a hydroxyl-substituted sulfur-containing compound.

In various embodiments, the sulfur-containing compound is in a hydrocarbon mixture. For example, the sulfur-containing compound can be in a mixture with a fossil fuel, natural gas, petroleum, coal, crude oil or refined oil. In various embodiments, the sulfur-containing compound is in a waste stream. The waste stream may be an aqueous waste stream, an exhaust stream, or combustion and soot particulate.

The products of the reaction can be conclusively identified via gas chromatography-mass spectrometry (GC-MS) by comparison of measured retention times to known samples and/or by comparison of fragmentation patterns to publicly available mass spectra recorded in the National Institute of Standards and Technology (NIST) mass spectral database.

Oxidation

During the contacting to provide the oxidized product, the catalyst can have any suitable turnover number (e.g., the moles of product produced divided by the moles of catalyst used). For example, the turnover number can be about 200 to about 10,000, about 300 to about 1,000, about 500 to about 500, or about 200 or less, or about 250, 300, 350, 400, 450, 500, 550, 600, 650, 700, 750, 800, 850, 900, 950, 1,000, 1,100, 1,200, 1,300, 1,400, 1,500, 1,600, 1,800, 2,000, 2,500, 3,000, 4,000, 5,000, 6,000, 8,000, or about 10,000 or more. Any suitable amount of catalyst may be used. Typically, a catalytic or sub-stoichiometric amount of catalyst is used. In various embodiments, an amount of catalyst is used corresponding to any of the aforementioned turnover numbers, e.g., corresponding to a turnover number of about 200 to about 10,000.

During the contacting to provide the oxidized product, the catalyst can have any suitable turnover frequency (e.g., turnover number divided by reaction time). For example, the turnover frequency can be about 500 $h^{-1}$ to about 20,000 $h^{-1}$, about 1,000 $h^{-1}$ to about 4,000 $h^{-1}$, about 500 $h^{-1}$ or less, or about 600 $h^{-1}$, 800, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,500, 4,000, 4,500, 5,000, 6,000, 7,000, 8,000, 9,000, 10,000, 15,000, or about 20,000 $h^{-1}$ or more. In various embodiments, the reaction may result in complete conversion of the oxidizable starting material to an oxidation product or may result in 80%, 85%, 90%, 95%, 96%, 97%, 98%, 99%, 99.5%, 99.9%, 99.99% conversion of the oxidizable starting material to an oxidation product. In various embodiments, complete or near complete conversion may be achieved in about 5 minutes or more, in about 30 minutes to about 2 hours, in under or about an hour, in under or about 2 hours, in under or about 3 hours, in under or about 5 hours, in under or about 10 hours, in under or about 12 hours, or in under or about a day. In various embodiments, the catalyst is contacted with the sulfur-containing compound for at least 1, 2, 3, 4, 5, 6, 7, 8, 9, 10, 15, 30, or 45 minutes. In various embodiments, the catalyst is contacted with the sulfur-containing compound for at least 0.1, 0.2, 0.3, 0.4, 0.5, 0.6, 0.7, 0.8, 0.9, 1, 2, 3, 4, 5, 6, 7, 8, 9, or 10 hours.

In various embodiments, the oxidation is performed at room temperature.

In some embodiments, the sulfur-containing compound is a sulfoxide which is oxidized to a sulfone. In some embodiments, the sulfur-containing compound is a sulfide which is oxidized to a disulfide. In some embodiments, the sulfur-containing compound is oxidized to a sulfate.

In various embodiments, the sulfur-containing compound has a terminal —SH group and the product is a disulfide. In various embodiments, the sulfur-containing compound has a divalent —S— group, and the product is a sulfone or sulfoxide. In various embodiments, the initial sulfur-containing compound is a divalent —S— group which is directly substituted with one or two aryl groups, one or two alkyl groups, or one alkyl group and one aryl group. In various embodiments, the initial sulfur-containing compound has a terminal —SH. In some embodiments, the sulfur-containing compound is $H_2S$.

In various embodiments, the sulfur-containing compound is preferentially oxidized at sulfur. The sulfur-containing compound in some embodiments may preferentially oxidize in the presence of alcohols.

Oxidation may be performed at any suitable temperature. In various embodiments, oxidation is performed at temperatures including room temperature. In various embodiments, oxidation is performed at a temperature of from about 10° C. to about 30° C. In various embodiments, oxidation is performed at room temperature or higher. In various embodiments, oxidation is performed at a temperature of less than or about 40° C., 50° C., 60° C., 70° C., 80° C., 90° C. or 100° C. In various embodiments, oxidation may be performed up to the boiling point of the solvent or starting material. In various embodiments, oxidation is performed without any external cooling or heating. In various embodiments, the oxidation is performed at ambient pressure. In various embodiments, the oxidation is performed at least or about 0.8 atm to at least or about 1 atm. In various embodiments, the oxidation is performed at ambient temperature.

Various embodiments described herein can be performed using only ambient air, at ambient pressure and temperature. In various embodiments, the predominantly involved oxidant is molecular oxygen in air. In various embodiments, the sole oxidant is molecular oxygen in air. In various embodiments, no additional oxidant is added. For example, no peroxides, chlorites, chlorites, perchlorates, nitrates, chromium compounds, permanganate compounds, perborates, and the like, are added. In some embodiments, the fluid upon which the catalyst acts may be free of peroxides, chlorates, chlorites, perchlorates, nitrates, chromium compounds, permanganate compounds, perborates, and the like. In some embodiments, no other oxidant is present other than ambient air.

In various embodiments, the sulfur-containing compounds are present in a natural gas, a waste stream, a sewage mixture, a crude oil, or a refined oil. For example, the sulfur-containing compound may be present in a waste stream from papermaking or sewage treating operations. Such sources of sulfur-containing compounds may be the media which is being treated for removal of mercaptan compounds.

The various embodiments described herein can be useful and effective for the removal of undesired sulfur-containing compounds from liquid mixtures, gaseous mixtures, or both. For example, the liquid mixture or gaseous mixtures may be one or more of a crude oil, a refined oil, a natural gas, an aqueous solution, an organic solution, and a waste stream.

EXAMPLES

Various embodiments of the present invention can be better understood by reference to the following Examples which are offered by way of illustration. The present invention is not limited to the Examples given herein.

Materials

Catalysts A and B were prepared according to the methods described in U.S. Patent Application Publication No. 2017/0022233 A1, which is incorporated by reference in its entirety. Starting materials and solvents may be obtained from Sigma-Aldrich (St. Louis, MO) or other chemical suppliers.

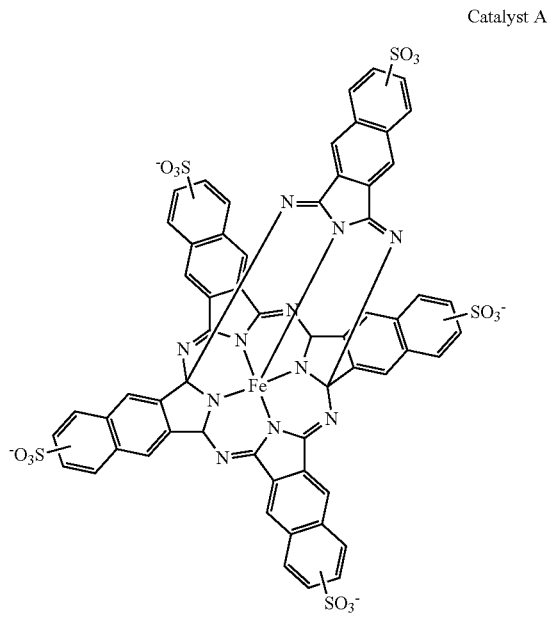

Catalyst A

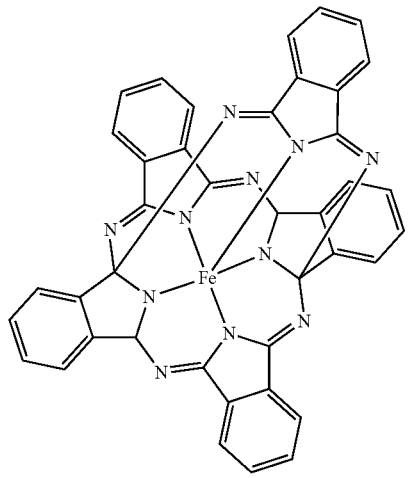

Catalyst B

Example 1

Oxidation of 2-Mercaptoethanol Using Catalyst A (Na$^+$ Salt) at Room Temperature with Hydrogen Peroxide 2-Mercaptoethanol was treated with the sodium-salt form of Catalyst A using hydrogen peroxide oxidant as the primary oxidant. The reaction was conducted in a mixed water/ethanol solution at room temperature and provided 2-hydroxyethyl disulfide (also known as bis(2-hydroxyethyl) disulfide and 2,2'-dithiodiethanol) as the product. The reaction proceeded to 100% and gave a turnover number (TON) of about 2800.

Example 2

Oxidation of 2-Mercaptoethanol Using Catalyst A (Na$^+$ Salt) at Room Temperature with Molecular Oxygen from Ambient Air 2-Mercaptoethanol was treated with the sodium-salt form of Catalyst A in the presence of molecular oxygen from ambient air as the primary oxidant. The reaction was conducted in a mixed water/ethanol solution at room temperature and provided 2-hydroxyethyl disulfide as the sole product. The reaction proceeded to near completion in 2 hours.

Example 3

Oxidation of 2-Mercaptoethanol Using Catalyst A (Immobilized on Ion-Exchange Resin) at Room Temperature with Molecular Oxygen from Ambient Air 2-Mercaptoethanol was treated with Catalyst A immobilized on AMBERLITE® ion-exchange resin in the presence of molecular oxygen from ambient air as the primary oxidant. The reaction was conducted in a mixed water/ethanol solution at room temperature and provided 2-hydroxyethyl disulfide as the sole product. The reaction proceeded to 100% completion in about 12 hours and gave an estimated TON of about 2400. The TON was estimated assuming all catalytic sites were available for the immobilized catalyst. However, if immobilization blocks some catalytic sites, then the actual TON would be higher.

Example 4

Oxidation of 2-Mercaptoethanol Using Catalyst B at Room Temperature with Hydrogen Peroxide 2-Mercaptoethanol was treated with Catalyst B using hydrogen peroxide as the primary oxidant. The reaction was conducted in a n-propanol solution at room temperature and provided 2-hydroxyethyl disulfide as the sole product in n-propanol solution. The reaction proceeded to 100% completion in about 40 minutes and gave a TON of about 1500.

Example 5

Oxidation of 2-Mercaptoethanol Using Catalyst B at Room Temperature with Molecular Oxygen from Ambient Air 2-Mercaptoethanol was treated with Catalyst B in the presence of molecular oxygen from ambient air as the primary oxidant. The reaction was conducted in a n-propanol solution at room temperature and provided 2-hydroxyethyl disulfide as the sole product in n-propanol solution. The reaction proceeded to 100% completion in about 3 hours and gave a TON of about 1300.

Example 6

Oxidation of 2-Mercaptoethanol Using Catalyst A (Immobilized on Amino-Modified Silica Gel) at Room Temperature with Hydrogen Peroxide 2-Mercaptoethanol was treated with Catalyst A supported on amino-modified silica gel using hydrogen peroxide as the primary oxidant. The reaction was conducted in a mixed water/ethanol solution at room temperature and provided 2-hydroxyethyl disulfide as the sole product. The reaction proceeded to 100% completion in about 2 hours and gave an estimated TON of about 4500. The TON was estimated assuming all catalytic sites were available for the immobilized catalyst. However, if immobilization blocks some catalytic sites, then the actual TON would be higher.

Example 7

Oxidation of Dibenzothiophene Using Catalyst B at Room Temperature with Hydrogen Peroxide Dibenzothiophene was treated with Catalyst B using hydrogen peroxide as the primary oxidant. The reaction was conducted in a mixed acetonitrile/dichloromethane solution at room temperature and provided dibenzothiophene 5,5-dioxide. During the course of the reaction, dibenzothiophene 5-oxide was intermediately formed and consumed to provide the final product. The reaction proceeded to complete conversion of dibenzothiophene to dibenzothiophene 5,5-dioxide and gave a TON of about 700. The reaction was monitored and product conclusively identified via gas chromatography-mass spectrometry (GC-MS) via comparison of measured retention times to known samples and fragmentation patterns to publicly available mass spectra recorded in the National Institute of Standards and Technology (NIST) mass spectral database.

Example 8

Oxidation of Ethyl Mercaptan Using Catalyst A in Aqueous-Organic Solvent at Room Temperature Using Molecular Oxygen from Ambient Air as the Primary Oxidant A 0.27 mM solution of Catalyst A was combined with ethyl mercaptan having an initial concentration of a 0.45 M. This solution was a mixed ethanol/water solution, which was stirred while open to ambient air over the course of four hours. No additional oxidant was added. The only product in greater than trace amount in solution was diethyl disulfide (also known as ethyl disulfide).

Example 9

Oxidation of Ethyl Mercaptan Using Catalyst B in Ethanol at Room Temperature Using Molecular Oxygen from Ambient Air as the Primary Oxidant A 0.9 mM solution of catalyst B was combined with ethyl mercaptan having an initial concentration of a 0.54 M. This solution was an ethanol solution, which was stirred while open to ambient air over the course of four hours. No additional oxidant was added. The only product in greater than trace amount in solution was diethyl disulfide.

Example 10

Oxidation of Ethyl Mercaptan Using Catalyst B in Butanol at Room Temperature Using Molecular Oxygen from Ambient Air as the Primary Oxidant A 0.42 mM solution of catalyst B was combined with ethyl mercaptan having an initial concentration of a 0.54 M. This solution was a 1-butanol solution, which was stirred while open to ambient air over the course of six hours. No additional oxidant was added. The only product in greater than trace amount in solution was diethyl disulfide.

Example 11

Oxidation of Vapor-Phase Ethyl Mercaptan Using Catalyst B at Room Temperature Using Molecular Oxygen from Ambient Air as the Primary Oxidant A 0.77 mM solution of catalyst B in ethanol was vigorously stirred while open to ambient air and mercaptan vapor. This solution was a 1-butanol solution, which was stirred while open to ambient air over the course of six hours. Gas chromatography-mass spectrometry (GC-MS) identified diethyl disulfide as the only product present in any significant amount.

Example 12

Oxidation of Propyl Mercaptan Using Catalyst A in Aqueous-Organic Solvent at Room Temperature Using Molecular Oxygen from Ambient Air as the Primary Oxidant A 0.30 M solution of Catalyst A was combined with n-propyl mercaptan having an initial concentration of a 0.28 M. This solution was a mixed ethanol/water solution, which was stirred while open to ambient air over the course of seven hours. No additional oxidant was added. The only product in greater than trace amount in solution was dipropyl disulfide (also known as n-propyl disulfide).

Example 13

Oxidation of Propyl Mercaptan Using Catalyst B in Ethanol Solvent at Room Temperature Using Molecular Oxygen from Ambient Air as the Primary Oxidant A solution of Catalyst B was combined with n-propyl mercaptan having an initial concentration of a 0.44 M. This solution was an ethano solution, which was stirred while open to ambient air over the course of six hours. No additional oxidant was added. The only product in greater than trace amount in solution was dipropyl disulfide.

Example 14

Oxidation of Ethyl Mercaptan Using Catalyst B in a Biphasic Solvent System Containing Tetradecane and Ethanol at Room Temperature Using Molecular Oxygen from Ambient Air as the Primary Oxidant A solution of Catalyst B (3.0 mg, 0.0037 mmol) in ethanol (5.0 mL) was combined with ethyl mercaptan (4.05 mmol) and tetradecane (5.0 mL). Tetradecane is a long-chain nonpolar hydrocarbon that models crude oil. A biphasic mixture resulted, which was vigorously stirred open to ambient air at room temperature. No additional oxidant was added. GC-MS analysis of both the upper (tetradecane) and lower (ethanol) phases showed the presence of diethyl disulfide, which was the only product in greater than trace amount in solution. The oxidized mercaptan product (diethyl disulfide) was readily removed from the oil phase. GC-MS analysis showed complete removal of the mercaptan from the non-polar (tetradecane) phase, demonstrating that Catalyst B is an effective catalyst for the removal of mercaptans dissolved in non-polar hydrocarbons such as unrefined petroleum.

Example 15

Oxidation of Dibenzothiophene Using Catalyst B in a Biphasic Solvent System Containing Tetradecane and Ethanol at Room Temperature with Hydrogen Peroxide A solution of Catalyst B (3.5 mg, 0.0043 mmol) in ethanol (5.0 mL) was combined with dibenzothiophene (61.3 mg, 0.333 mmol) in tetradecane (10.0 mL) resulting in a biphasic mixture. Tetradecane is a long-chain non-polar hydrocarbon that models crude oil. This biphasic mixture was treated with 2.0 mL of 30% hydrogen peroxide solution in water at room temperature with stirring. Analysis of the lower (ethanol) phase showed the presence of dibenzothiophene 5,5-dioxide, with a trace of the starting dibenzothiophene substrate. Analysis of the upper (tetradecane) phase showed only a trace of the (polar) dibenzothiophene 5,5-dioxide product with some remaining dibenzothiophene. The oxidized product (dibenzothiophene 5,5-dioxide) is removed from the oil phase by partition into the more polar phase. This experiment demonstrates that Catalyst B is effective to catalyzes the conversion of dibenzothiophene and similar compounds in non-polar hydrocarbons such as unrefined petroleum.

These examples demonstrated effective removal of mercaptans from a given media, both liquid and gaseous, via oxidation of the mercaptans to disulfides.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

ADDITIONAL EMBODIMENTS

The following exemplary embodiments are provided, the numbering of which is not to be construed as designating levels of importance:

Embodiment 1 provides a method of oxidizing a sulfur-containing compound, comprising:

contacting the sulfur-containing compound with a catalyst in the presence of an oxidant, the catalyst having the structure:

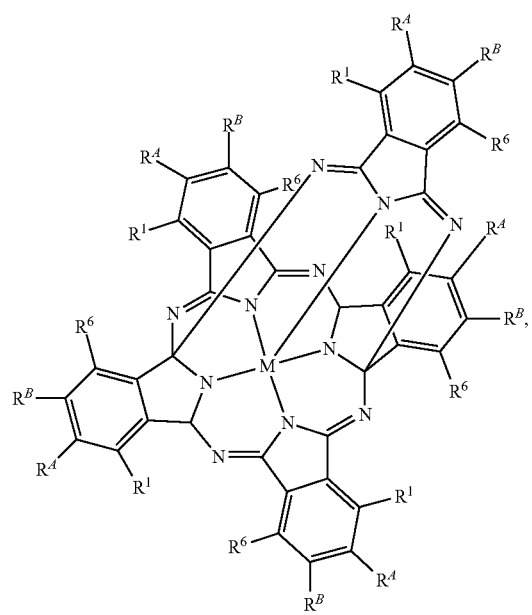

wherein

M is a metal, axial ligand L is a solvent molecule or absent, at each occurrence, $R^A$ and $R^B$ are independently chosen from —H, halide, an organic group, and a hydrophilic group, or $R^A$ and $R^B$ together form a fused aromatic ring with the ring upon which $R^A$ and $R^B$ are substituted, $R^A$ and $R^B$ together having the structure:

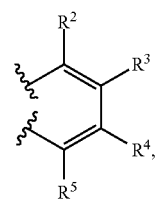

at each occurrence, $R^1$, $R^2$, $R^3$, $R^4$, $R^5$, and $R^6$ are each independently chosen from —H, halide, an organic group, and a hydrophilic group, a salt thereof, a substituted or unsubstituted ($C_1$-$C_{50}$)hydrocarbyl ester thereof, and a combination thereof.

Embodiment 2 provides the method of Embodiment 1, wherein the only oxidant present in stoichiometric or greater quantities is molecular oxygen of ambient air.

Embodiment 3 provides the method of Embodiment 1 or 2, wherein the catalyst has the structure:

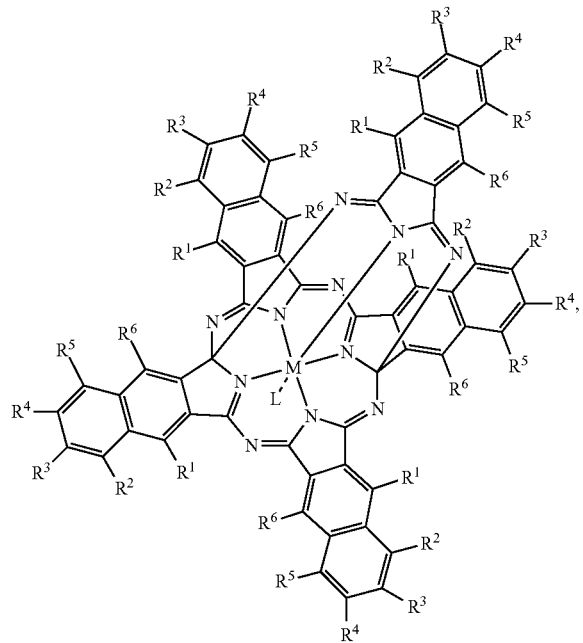

wherein
M is a metal,
L is a solvent molecule or absent, and
at each occurrence, $R^1$, $R^2$, $R^3$, $R^4$, $R^5$, and $R^6$ are independently chosen from —H, halide, an organic group, and a hydrophilic group.

Embodiment 4 provides the method of any combination of Embodiments 1-3, wherein at each occurrence, the hydrophilic group is independently chosen from —C(O)OH, —O—C(O)OH, —P(O)(OH)$_2$, —OP(O)(OH)$_2$, —S(O)(O)OH, —OS(O)(O)OH, a salt thereof, a substituted or unsubstituted ($C_1$-$C_{50}$)hydrocarbyl ester thereof, and a combination thereof.

Embodiment 5 provides the method of any combination of Embodiments 1-4, wherein at least one of $R^2$, $R^3$, $R^4$, and $R^5$ is —S(O)(O)OH.

Embodiment 6 provides the method of any combination of Embodiments 1-5, wherein the catalyst has the structure:

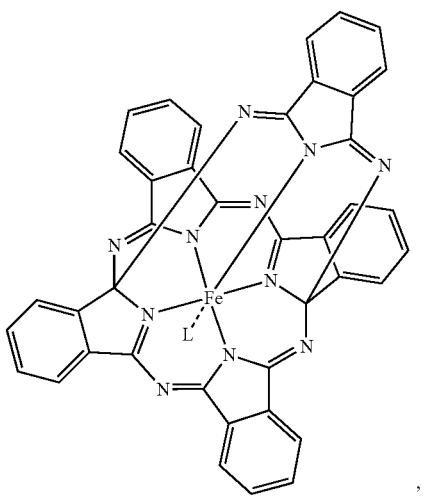

wherein axial ligand L is $H_2O$.

Embodiment 7 provides the method of any combination of Embodiments 1-5, wherein the catalyst has the structure:

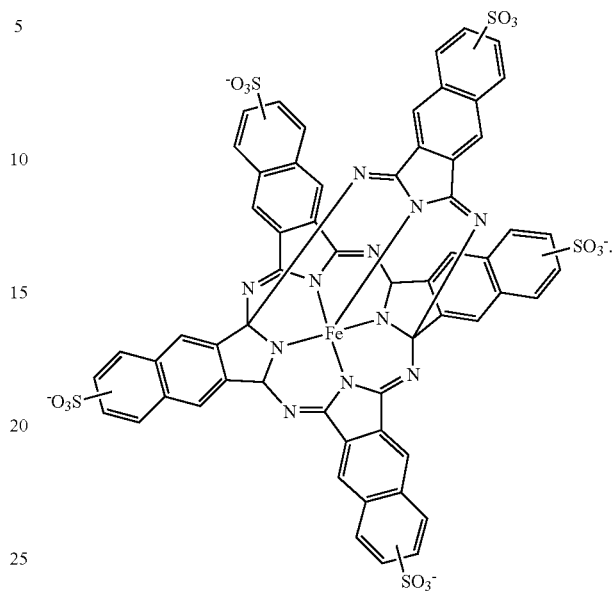

Embodiment 8 provides the method of any combination of Embodiments 1-5, wherein the catalyst has the structure:

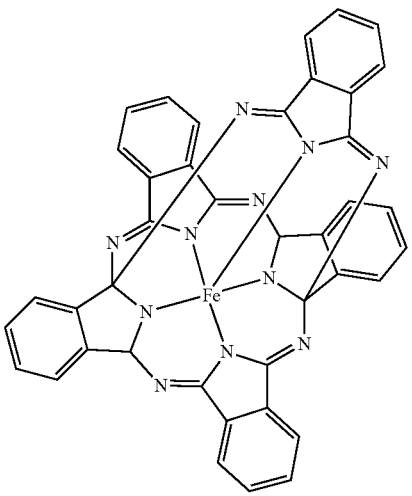

Embodiment 9 provides the method of any combination of Embodiments 1-8, wherein the contacting is performed at room temperature.

Embodiment 10 provides the method of any combination of Embodiments 1-9, wherein the sulfur-containing compound and catalyst are contacted in the presence of solvent.

Embodiment 11 provides the method of any combination of Embodiments 1-10, wherein the sulfur-containing compound and catalyst are contacted in the absence of solvent.

Embodiment 12 provides the method of any combination of Embodiments 1-11, wherein the solvent comprises water.

Embodiment 13 provides the method of any combination of Embodiments 1-12, wherein the solvent comprises $C_1$-$C_{10}$ alcohol.

Embodiment 14 provides the method of any combination of Embodiments 1-13, wherein the solvent comprises ethanol or n-propanol.

Embodiment 15 provides the method of any combination of Embodiments 1-14, wherein the solvent comprises one or more of acetonitrile and dichloromethane.

Embodiment 16 provides the method of any combination of Embodiments 1-15, wherein the sulfur-containing compound has the structure

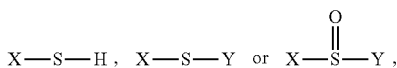

wherein each of X and Y is independently $C_1$-$C_{20}$ alkyl, $C_6$-$C_{10}$ aryl or $C_2$-$C_{10}$ heteroaryl, each of which may be optionally substituted, and X and Y may be linked so as to form a ring.

Embodiment 17 provides the method of any combination of Embodiments 1-16, wherein the sulfur-containing compound is an aromatic thiol, a non-aromatic thiol or a thioether.

Embodiment 18 provides the method of any combination of Embodiments 1-17, wherein the sulfur-containing compound is a substituted or unsubstituted alkylthiol.

Embodiment 19 provides the method of any combination of Embodiments 1-18, wherein the sulfur-containing compound is

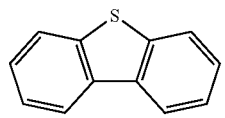

Embodiment 20 provides the method of any combination of Embodiments 1-19, wherein the sulfur-containing compound is

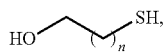

wherein n is 0-10.

Embodiment 21 provides the method of any combination of Embodiments 1-20, wherein the catalyst is homogeneous.

Embodiment 22 provides the method of any combination of Embodiments 1-20, wherein the catalyst is heterogeneous.

Embodiment 23 provides the method of Embodiment 22, wherein the catalyst is immobilized on a solid support.

Embodiment 24 provides the method of Embodiment 23, wherein the solid support comprises silica, zeolite, ion-exchange resin, or sulfonated polystyrene.

Embodiment 25 provides a method of removing sulfur-containing compounds from a fluid, comprising:
  contacting the fluid with a catalyst in the presence of an oxidant to produce an oxidized sulfur-containing compound; and then
  separating the oxidized sulfur-containing compound from the fluid, wherein the catalyst has the structure

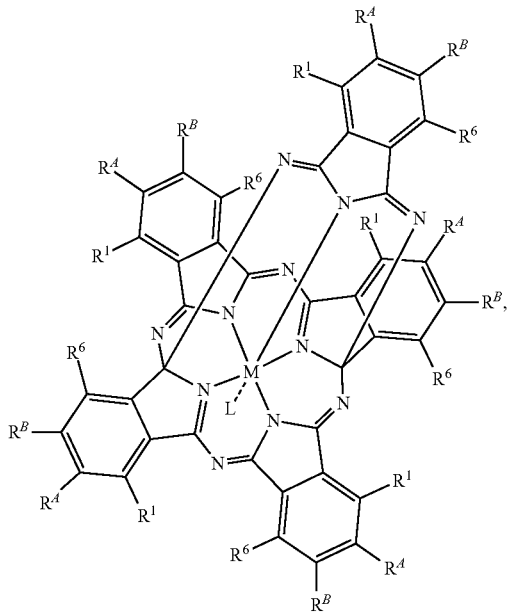

wherein
  M is a metal,
  axial ligand L is a solvent molecule or absent,
  at each occurrence, $R^A$ and $R^B$ are independently chosen from —H, halide, an organic group, and a hydrophilic group, or $R^A$ and $R^B$ together form a fused aromatic ring with the ring upon which $R^A$ and $R^B$ are substituted, $R^A$ and $R^B$ together having the structure:

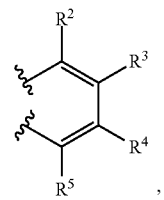

and at each occurrence, $R^1$, $R^2$, $R^3$, $R^4$, $R^5$, and $R^6$ are each independently chosen from —H, halide, an organic group, and a hydrophilic group, a salt thereof, a substituted or unsubstituted ($C_1$-$C_{50}$)hydrocarbyl ester thereof, and a combination thereof.

Embodiment 26 provides the method of Embodiment 25, wherein the fluid is crude oil, a refined oil, a hydrocarbon mixture, a fossil fuel, a natural gas, petroleum, coal, an aqueous waste stream, an exhaust gas waste stream, a combustion gas waste stream, a combusted crude oil, a combusted refined oil, a combusted hydrocarbon mixture, a combusted fossil fuel, a combusted natural gas, combusted petroleum, combusted coal, or a mixture thereof.

Embodiment 27 provides the method of Embodiments 25 or 26, wherein the separating step comprising mixing the fluid with a immiscible solvent having greater affinity than the fluid for the oxidized sulfur-containing compound.

Embodiment 28 provides the method of any combination of Embodiments 25-27, wherein the separating step comprises filtration, distillation, or chromatography of the fluid containing the oxidized sulfur-containing compound.

Embodiment 29 provides the method of any combination of Embodiments 25-28, wherein the contacting step is performed at room temperature.

Embodiment 30 provides the method of any combination of Embodiments 25-29, wherein the oxidant is molecular oxygen in ambient air.

Embodiment 31 provides the method of any combination of Embodiments 25-30, wherein the oxidant is molecular oxygen in ambient air and no other oxidant is present in stoichiometric or greater quantities Embodiment 32 provides the catalyst or method of any one or any combination of Embodiments 1-30 optionally configured such that all elements or options recited are available to use or select from.

What is claimed is:

1. A method of oxidizing a sulfur-containing compound, comprising:
contacting the sulfur-containing compound with a catalyst in the presence of an oxidant, the catalyst having the structure:

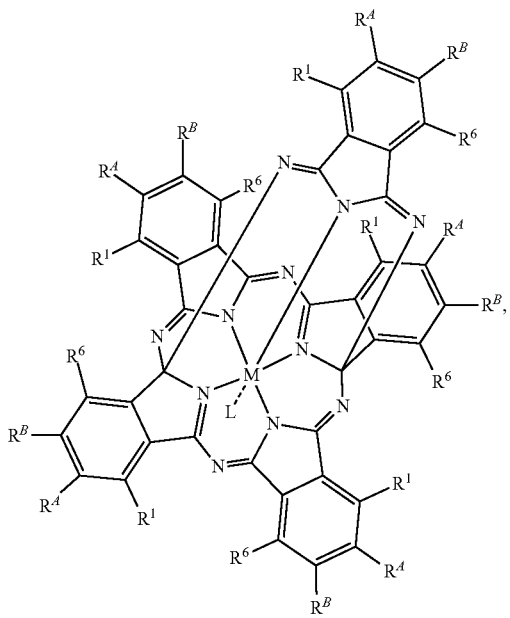

wherein
M is a metal,
axial ligand L is a solvent molecule or absent,
at each occurrence, $R^A$ and $R^B$ are independently chosen from —H, halide, an organic group, and a hydrophilic group, or $R^A$ and $R^B$ together form a fused aromatic ring with the ring upon which $R^A$ and $R^B$ are substituted, $R^A$ and $R^B$ together having the structure:

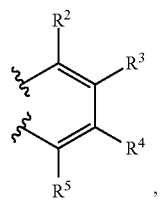

and
at each occurrence, $R^1$, $R^2$, $R^3$, $R^4$, $R^5$, and $R^6$ are each independently chosen from —H, halide, an organic group, a hydrophilic group, a salt thereof, a substituted or unsubstituted $(C_1\text{-}C_{50})$hydrocarbyl ester thereof, and a combination thereof, and wherein the sulfur-containing compound is a thioether or has the structure

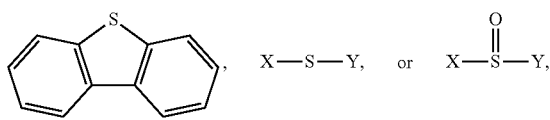

wherein each of X and Y is independently $C_1\text{-}C_{20}$ alkyl, $C_6\text{-}C_{10}$ aryl or $C_2\text{-}C_{10}$ heteroaryl, each of which may be optionally substituted, wherein X and Y are optionally linked so as to form a ring.

2. The method of claim 1, wherein the only oxidant present in stoichiometric or greater quantities is molecular oxygen of ambient air.

3. The method of claim 1, wherein the catalyst has the structure:

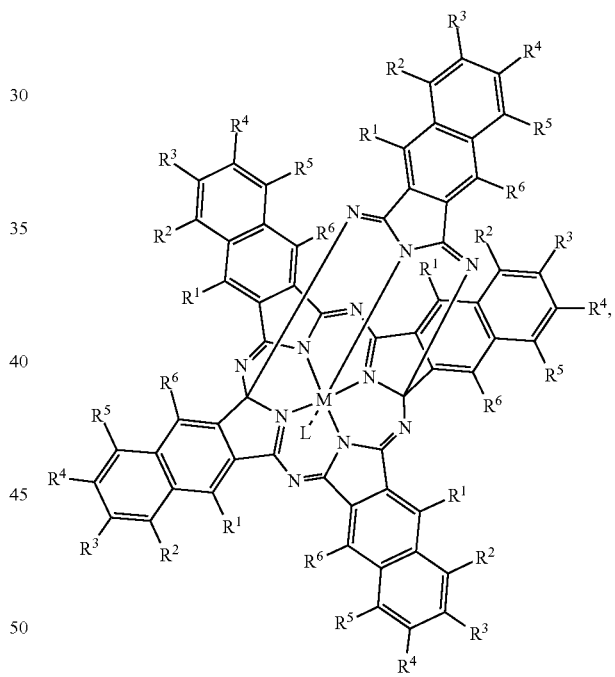

wherein
M is a metal,
L is a solvent molecule or absent, and
at each occurrence, $R^1$, $R^2$, $R^3$, $R^4$, $R^5$, and $R^6$ are independently chosen from —H, halide, an organic group, and a hydrophilic group.

4. The method of claim 1, wherein at each occurrence, the hydrophilic group is independently chosen from —C(O)OH, —O—C(O)OH, —P(O)(OH)$_2$, —OP(O)(OH)$_2$, —S(O)(O)OH, —OS(O)(O)OH, a salt thereof, a substituted or unsubstituted $(C_1\text{-}C_{50})$hydrocarbyl ester thereof, and a combination thereof.

5. The method of claim 1, wherein the catalyst has the structure:

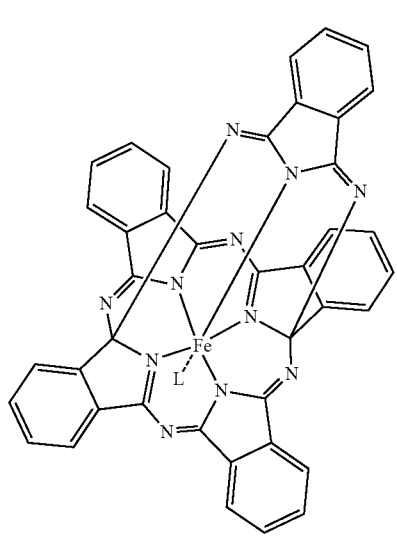

wherein axial ligand L is $H_2O$.

6. The method of claim 1, wherein the catalyst has the structure:

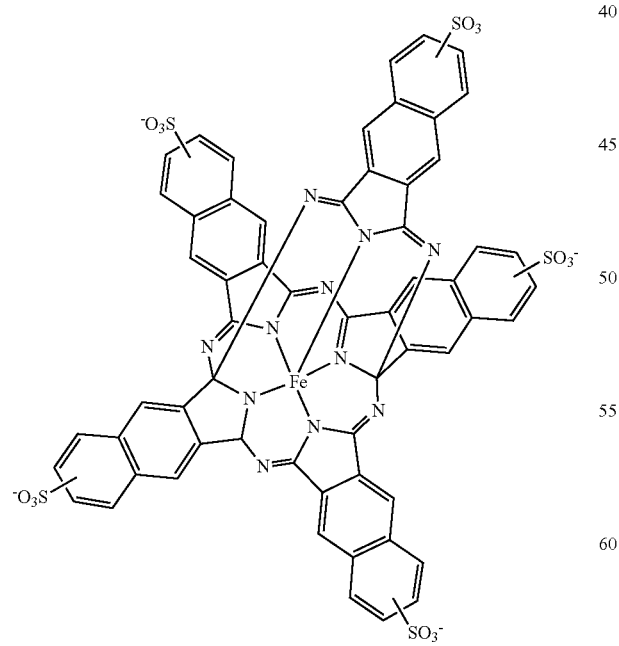

in salt form, or

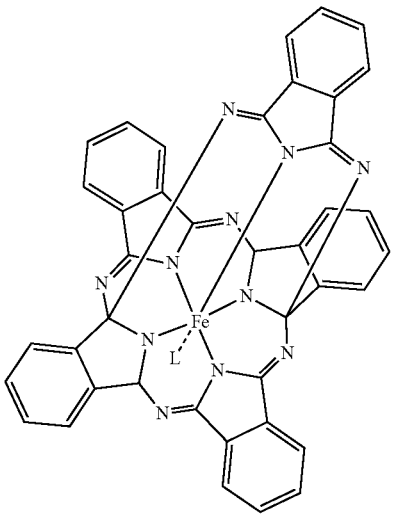

7. The method of claim 1, wherein the contacting is performed at room temperature.

8. The method of claim 1, wherein the sulfur-containing compound is in solution.

9. The method of claim 1, wherein the sulfur-containing compound is in the vapor phase.

10. The method of claim 1, wherein the sulfur-containing compound is in a crude oil, a refined oil, a natural gas, an aqueous waste stream, an exhaust gas waste stream, a combustion gas waste stream, or a mixture thereof.

11. The method of claim 1, wherein the solvent comprises water, $C_1$-$C_{10}$ alcohol, non-polar organic solvent, or a combination thereof.

12. The method of claim 1, wherein the sulfur-containing compound is a thioether.

13. The method of claim 1, wherein the sulfur-containing compound is

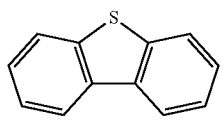

14. A method of removing sulfur-containing compounds from a fluid, comprising:
  contacting the fluid and sulfur-containing compounds with a catalyst in the presence of an oxidant to produce an oxidized sulfur-containing compound; and then
  separating the oxidized sulfur-containing compound from the fluid, wherein
  the catalyst has the structure

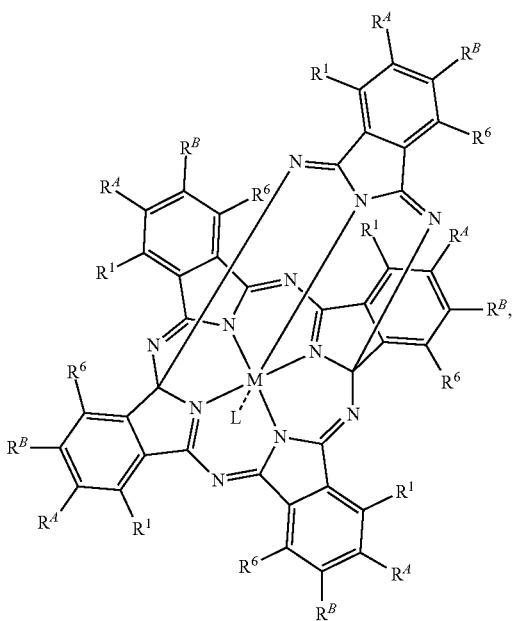

wherein
M is a metal,
axial ligand L is a solvent molecule or absent,
at each occurrence, $R^A$ and $R^B$ are independently chosen from —H, halide, an organic group, and a hydrophilic group, or $R^A$ and $R^B$ together form a fused aromatic ring with the ring upon which $R^A$ and $R^B$ are substituted, $R^A$ and $R^B$ together having the structure:

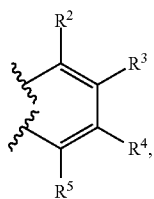

and
at each occurrence, $R^1$, $R^2$, $R^3$, $R^4$, $R^5$, and $R^6$ are each independently chosen from —H, halide, an organic group, a hydrophilic group, a salt thereof, a substituted or unsubstituted $(C_1\text{-}C_{50})$hydrocarbyl ester thereof, and a combination thereof; and wherein contacting the fluid and the sulfur-containing compounds to produce the oxidized sulfur-containing compound comprises producing the oxidized sulfur-containing compound from a compound that is a thioether or that has the structure

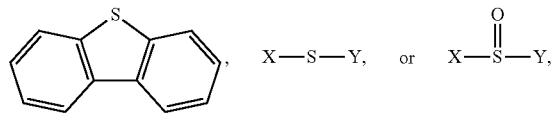

wherein each of X and Y is independently $C_1\text{-}C_{20}$ alkyl, $C_6\text{-}C_{10}$ aryl or $C_2\text{-}C_{10}$ heteroaryl, each of which may be optionally substituted, wherein X and Y are optionally linked so as to form a ring.

15. The method of claim 14, wherein the fluid is a crude oil, a refined oil, a hydrocarbon mixture, a fossil fuel, a natural gas, petroleum, coal, an aqueous waste stream, an exhaust gas waste stream, a combustion gas waste stream, a combusted crude oil, a combusted refined oil, a combusted hydrocarbon mixture, a combusted fossil fuel, a combusted natural gas, combusted petroleum, combusted coal, or a mixture thereof.

16. The method of claim 14, wherein the fluid is a liquid, a gas, or a mixture thereof.

17. The method of claim 14, wherein the contacting step is performed at room temperature.

18. The method of claim 14, wherein the oxidant is molecular oxygen in ambient air and no other oxidant is present in stoichiometric or greater quantities.

19. The method of claim 1, wherein contacting the sulfur-containing compound with the catalyst comprises contacting a composition comprising the sulfur-containing compound with the catalyst, wherein the composition further comprises an aromatic thiol, a non-aromatic thiol, a substituted or unsubstituted alkylthiol,

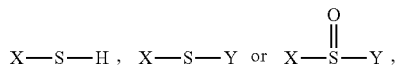

or a combination thereof, wherein X is $C_1\text{-}C_{20}$ alkyl, $C_6\text{-}C_{10}$ aryl, or $C_2\text{-}C_{10}$ heteroaryl, n is 0-10, and m is 0-10.

* * * * *

UNITED STATES PATENT AND TRADEMARK OFFICE
CERTIFICATE OF CORRECTION

PATENT NO. : 12,134,593 B2
APPLICATION NO. : 17/268311
DATED : November 5, 2024
INVENTOR(S) : Robert William McGaff It is certified that error appears in the above-identified patent and that said Letters Patent is hereby corrected as shown below:

On the Title Page

In Column 2, under item (56) "Other Publications", Line 34, delete "ligand{"," and insert --ligand†",-- therefor On page 2, in Column 1, under item (56) "Other Publications", Line 7, delete "solventt"," and insert --solvent†",-- therefor In the Claims In Column 46, Line 3, in Claim 1, delete "thereof," and insert --thereof;-- therefor In Column 48, Lines 53-57, in Claim 13, after " 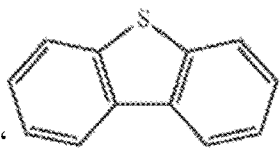 ", insert --.--

In Column 48, Line 67, in Claim 14, after "structure", insert --:--

Signed and Sealed this
Twenty-eighth Day of October, 2025

John A. Squires
*Director of the United States Patent and Trademark Office*